(12) United States Patent
Sohn et al.

(10) Patent No.: US 11,491,132 B2
(45) Date of Patent: *Nov. 8, 2022

(54) METHODS FOR TREATING THROMBOCYTOPENIA

(71) Applicant: Enzychem Lifesciences Corporation, Seoul (KR)

(72) Inventors: Ki-Young Sohn, Seoul (KR); Jae Wha Kim, Seoul (KR)

(73) Assignee: Enzychem Lifesciences Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/775,886

(22) Filed: Jan. 29, 2020

(65) Prior Publication Data

US 2020/0289451 A1 Sep. 17, 2020

Related U.S. Application Data

(63) Continuation of application No. 14/951,353, filed on Nov. 24, 2015, now Pat. No. 10,596,141, which is a continuation of application No. PCT/US2015/031204, filed on May 15, 2015.

(60) Provisional application No. 62/083,749, filed on Nov. 24, 2014, provisional application No. 62/083,739, filed on Nov. 24, 2014, provisional application No. 62/018,528, filed on Jun. 27, 2014, provisional application No. 62/018,530, filed on Jun. 27, 2014, provisional application No. 61/993,784, filed on May 15, 2014, provisional application No. 61/993,774, filed on May 15, 2014.

(51) Int. Cl.
| | |
|---|---|
| *A61K 31/231* | (2006.01) |
| *A61K 9/48* | (2006.01) |
| *A61K 31/23* | (2006.01) |
| *A61K 31/7048* | (2006.01) |
| *A61K 31/454* | (2006.01) |
| *A61K 31/185* | (2006.01) |
| *A61K 45/06* | (2006.01) |
| *A61K 31/704* | (2006.01) |
| *A61K 31/355* | (2006.01) |
| *A61K 31/138* | (2006.01) |
| *A61K 31/675* | (2006.01) |
| *A61K 33/243* | (2019.01) |
| *A61K 9/00* | (2006.01) |
| *A61K 38/19* | (2006.01) |

(52) U.S. Cl.
CPC .......... *A61K 31/231* (2013.01); *A61K 9/0053* (2013.01); *A61K 9/4825* (2013.01); *A61K 31/138* (2013.01); *A61K 31/185* (2013.01); *A61K 31/23* (2013.01); *A61K 31/355* (2013.01); *A61K 31/454* (2013.01); *A61K 31/675* (2013.01); *A61K 31/704* (2013.01); *A61K 31/7048* (2013.01); *A61K 33/243* (2019.01); *A61K 38/193* (2013.01); *A61K 45/06* (2013.01); *A61K 9/4858* (2013.01)

(58) Field of Classification Search
None
See application file for complete search history.

(56) References Cited

U.S. PATENT DOCUMENTS

| | | |
|---|---|---|
| 7,662,853 B2 | 2/2010 | Kim |
| 2003/0166535 A1 | 9/2003 | Podolsky |
| 2004/0029893 A1 | 2/2004 | Lane |
| 2008/0194877 A1 | 8/2008 | Letari et al. |
| 2008/0200543 A1 | 8/2008 | Kim |
| 2009/0253923 A1 | 10/2009 | Lee et al. |
| 2010/0035989 A1 | 2/2010 | Schwartz et al. |
| 2010/0137435 A1 | 6/2010 | Kim |
| 2010/0279959 A1 | 11/2010 | Gagnon et al. |
| 2014/0171438 A1 | 6/2014 | Pan et al. |
| 2016/0128966 A1 | 5/2016 | Han et al. |
| 2016/0166528 A1 | 6/2016 | Kim et al. |
| 2017/0128404 A1 | 5/2017 | Sohn |

FOREIGN PATENT DOCUMENTS

| | | |
|---|---|---|
| EP | 1900364 A2 | 3/2008 |
| JP | 2012-530130 A | 11/2012 |
| KR | 10-2000-0071887 A | 11/2000 |
| KR | 10-2005-0103259 A | 10/2005 |
| KR | 10-2006-0047447 A | 5/2006 |
| KR | 10-0646781 B1 | 11/2006 |
| KR | 10-2007-0010841 A | 1/2007 |
| WO | 99/26640 A1 | 6/1999 |
| WO | 2005-112912 A1 | 12/2005 |
| WO | 2007/011150 A1 | 1/2007 |
| WO | 2010/061862 A1 | 6/2010 |
| WO | 2010/146578 A2 | 12/2010 |
| WO | 2015/026114 A1 | 2/2015 |

OTHER PUBLICATIONS

Gomez et al (Blood 110:281,2007—Abstract only) (Year: 2007).*
Chang et al (J Thromb and Haemost 5(Suppl 1):318-327, 2007) (Year: 2007).*
Examination Report, dated Sep. 5, 2016, in connection with related Australian Patent Application No. 2014309637, 3 pages.

(Continued)

*Primary Examiner* — Craig D Ricci
(74) *Attorney, Agent, or Firm* — Fox Rothschild LLP; Peter F. Corless

(57) ABSTRACT

The disclosure provides methods for treating, controlling or mitigating leukopenia (e.g. neutropenia) and/or thrombocytopenia, for example in the context of cancer chemotherapy, comprising administration of a monoacetyl-diacyl-glycerol compound, as well as compositions useful therefor.

18 Claims, 9 Drawing Sheets

(56) References Cited

OTHER PUBLICATIONS

Response, filed Jan. 23, 2017, to Examination Report, dated Sep. 5, 2016, in connection with related Australian Patent Application No. 2014309637, 19 pages.
Examination Report, dated Feb. 10, 2017, in connection with related Australian Patent Application No. 2014309637, 3 pages.
Response, filed Apr. 21, 2017, to Examination Report, dated Feb. 10, 2017, in connection with related Australian Patent Application No. 2014309637, 16 pages.
Notice of Acceptance, dated May 8, 2017, in connection with related Australian Patent Application No. 2014309637, 3 pages.
Examination Search Report, dated May 4, 2017, in connection with related Canadian Patent Application No. 2921845, 3 pages.
Extended European Search Report, dated Mar. 24, 2017, in connection with related European Patent Application No. 14837360.8, 5 pages.
Letter/Written Disclosure of the Supplemental Information Disclosure Statement for the referenced application, filed herewith on Aug. 4, 2017, 2 pages.
Letter/Written Disclosure of the Supplemental Information Disclosure Statement for the referenced application, filed herewith on Mar. 28, 2018, 2 pages.
Notice of Acceptance, dated Feb. 28, 2018, in connection with Australian Patent Application No. 2015258840, 3 pages.
Letter/Written Disclosure of the Supplemental Information Disclosure Statement for the referenced application, filed herewith on Mar. 1, 2018, 2 pages.
Inukai et al., "Leukemic cells with 11q23 translocations express granulocyte colony-stimulating factor (G-C SF) receptor and their proliferation is stimulated with G-CSF," Leukemia 12:382-389 (1998).
Kim, Dr. Sanghee, "[immune regulation] [deer antlers] [Rockpid] Clinical experiment result of Rockpid—splenic activity enhancing leukocyte, neutrophil and platelet level," published Apr. 18, 2014 [online]; retrieved Feb. 21, 2018 from: <URL:m.blog.naver.com/PostView.nhn?blogId=orry&logNo=80211409969&proxyReferer=http%3 A%2F%2Fwww.google.co.lum/o2Furl%3Fsa%3Dt%26rct%3Dj%26q%3D%26esrc%3Ds%26source <http://2Fwww.google.co> %3Dweb%26cd%3D1%26ved%3D0ahUKEwjz7060wrXVAhUGj5QKHVSaBkOQFggkMAA%26url%3Dhttp%253A%.
Machine generaled English translation of Korean Patent No. 10-0646781 (Patent Application No. KR 10-1999-0044781; Publication No. KR 10-2001-0037330), accessed from the Korean Intellectual Property Office on Feb. 28, 2018, 13 pages.
Machine generated English translation of International Patent Publication No. WO 2010/061862, generated from PatentScope on Feb. 21, 2018, 43 pages.
Notice of Preliminary Rejection, dated Aug. 2, 2017, in connection with corresponding Korean Patent Application No. KR 10-2016-7035244 [English translation and original document in Korean], 12 pages.
Office Action, dated Aug. 29, 2017, in connection with corresponding Japanese Patent Application No. 2017-512879 [English translation and original document in Japanese], 9 pages.
Response, submitted Feb. 21, 2018, to Examination Report, dated Jun. 9, 2017, in connection with corresponding Australian Patent Application No. 2015258840, 99 pages.
Yang et al., "Stimulatory Effects of Monoacetyldiglycerides on Hematopoiesis," Biol. Pharm. Bull. 27(7):1121-1125 (2004).
English language summary of Japanese Office Action dated Jan. 8, 2019 issued in counterpart JP Application 2018-073153.
Jeong et al., "1-Palmitoyl-2-linoleoyl-3-acetylrac-rac-glycerol (PLAG) attenuates gemcitabine-induced neutrophil extravasation," Cell & Bioscience, (2019) 9:4, pp. 1-15.
Office Action and partial English language summary thereof, dated Mar. 27, 2019 issued in counterpart Chinese Application 201580038245.6.
Office Action and English language summary, dated Feb. 4, 2019, issued in Russian Application No. 2016149232.

Yang, et al., "Stimulatory Effects of Monoacetyldiglycerides on Hematopoiesis," Biol. Pharm. Bull., vol. 27(7) (2004), pp. 1121-1125.
Kim et al., "Therapeutic potential of EC-18 as a chemotherapy adjuvant for 5-fluorouracil-induced neutropenia," AACR 2019 Annual Meeting Mar. 29-Apr. 13, 2019.
Response, filed May 1, 2018, to Extended European Search Report, dated Jan. 25, 2018, in connection with European Patent Application No. 15793591.7, 22 pages.
Final Office Action, dated Apr. 30, 2018, in connection with U.S. Appl. No. 14/936,464, 14 pages.
Letter/Written Disclosure of the Supplemental Information Disclosure Statement for the referenced application, filed herewith on Jul. 17, 2018, 2 pages.
Letter/Written Disclosure of the Supplemental Information Disclosure Statement for the referenced application, filed herewith on Apr. 20, 2018, 3 pages.
Rapidis et al., "Induction chemotherapy followed by concurrent chemoradiation in advanced squamous cell carcinoma of the head and neck: final results from a phase II study with docetaxel, cisplatin and 5-fluorouracil with a four-year follow-up," Oral Oncology 42:675-684 (2006).
Official Action, dated Mar. 22, 2018, in connection with corresponding Russian Patent Application No. 2016149232 [English translation and original document in Russian], 29 pages.
Letter/Written Disclosure of the Supplemental Information Disclosure Statement for the referenced application, filed herewith on Feb. 20, 2018, 2 pages.
Request for Continued Examination and Preliminary Amendment, filed Aug. 4, 2017, responsive to the Final Office Action, dated Apr. 4, 2017, in connection with U.S. Appl. No. 14/936,464, 22 pages.
Office Action, dated Oct. 16, 2017, in connection with U.S. Appl. No. 14/936,464, 14 pages.
Amendment and Response, filed Feb. 2, 2018, to Office Action, dated Oct. 16, 2017, in connection with U.S. Appl. No. 14/936,464, 31 pages.
Amendment and Response, filed Aug. 11, 2017, to Office Action, dated Feb. 14, 2017, in connection with related U.S. Appl. No. 15/048,732, 12 pages.
Notice of Allowance, dated Oct. 2, 2017, in connection with related U.S. Appl. No. 15/048,732, 12 pages.
Response, filed Oct. 12, 2017, to Examiner's Report, dated May 4, 2017, in connection with related Canadian Patent Application No. 2,921,845, 25 pages.
Response, filed Oct. 4, 2017, to Extended European Search Report, dated Mar. 24, 2017, in connection with related European Patent Application No. 14837360.8, 26 pages.
Extended European Search Report, dated Jan. 25, 2018, in connection with corresponding European Patent Application No. 15793591.7, 9 pages.
Al-Tonbary et al., "Vitamin E and N-Acetylcysteine as Antioxidant Adjuvant Therapy in Children with Acute Lymphoblastic Leukemia," Advances in Hematology, vol. 2009, Article ID 689639, 5 pages (2009).
Cao et al., "Purification and structural identification of an autoinducer for the luminescence system of Vibrio harveyi," JBC 264:21670-21676 (1989).
Jones et al., "A randomised pilot Phase II study of doxorubicin and cyclophosphamide (AC) or epirubicin and cyclophosphamide (EC) given 2 weekly with pegfilgrastim (accelerated) vs 3 weekly (standard) for women with early breast cancer," Brit. J. Cancer 100:305-310 (2009).
Kavanagh, "An overview of immunomodulatory intervention in rheumatoid arthritis," Drugs Today 35(4-5):275 (1999). Abstract, 2 pages.
Kim et al., "Auranofin blocks interieukin-6 signalling by inhibiting phosphorylation of JAK1 and STAT3," Immunology 122(4): 607-614 (2007).
Kim et al., "EC-18, a synthetic monoacetyldiacylglyceride, inhbits hematogenous metastasis of KIGB-5 biliary cancer cell in hamster model," Journal of Korean Medical Science 24:474-480 (2009).

(56) References Cited

OTHER PUBLICATIONS

Machine generated English language translation of Korean Publication No. KR 10-2005-0103259, published Oct. 27, 2005, accessed from Espacenet on Jun. 29, 2017, 15 pages.
Morstyn et al., "Treatment of chemotherapy-induced neutropenia by subcutaneously administered granulocyte colony-stimulating factor with optimization of dose and duration of therapy," J. Clin. Oncol. 7(10):1554-1562 (1989). Abstract, 2 pages.
Wambi et al., "Dietary Antioxidants Protect Hematopoietic Cells and Improve Animal Sunrival after Total-Body Irradiation," Radiat. Res. 169(4):384-396 (2008); 25 pages.
Zuckerman, "Hematopoietic Abnormalities in Patients With Cancer," Cancer Control J. Suppl. 5(2 Suppl 1):1-4 (1998).
Office Action, dated Sep. 22, 2016, in connection with U.S. Appl. No. 14/936,464, 16 pages.
Response, submitted Jan. 23, 2017, to Office Action, dated Sep. 22, 2016, in connection with U.S. Appl. No. 14/936,464, 39 pages.
Final Office Action, dated Apr. 4, 2017, in connection with U.S. Appl. No. 14/936,464, 20 pages.
International Search Report and Written Opinion, dated Aug. 5, 2015, in connection with corresponding International Patent Application No. PCT/US2015/031204, 10 pages.
International Preliminary Reporton Patentability, dated Nov. 15, 2016, in connection with corresponding International Patent Application No. PCT/US2015/031204, 8 pages.
Examination Report, dated Jun. 9, 2017, in connection with corresponding Australian Patent Application No. 2015258840, 5 pages.
Office Action, dated May 19, 2016, in connection with related U.S. Appl. No. 14/959,750, 33 pages.
Response, filed Aug. 19, 2016, to Office Action, dated May 19, 2016, in connection with related U.S. Appl. No. 14/959,750, 7 pages.
Final Office Action, dated Dec. 29, 2016, in connection with related U.S. Appl. No. 14/959,750, 29 pages.
Request for Continued Examination and Preliminary Amendment, filed Jun. 29, 2017, responsive to the Final Office Action, dated Dec. 29, 2016, in connection with related U.S. Appl. No. 14/959,750, 18 pages.
Notice of Allowance, dated Jul. 28, 2017, in connection with related U.S. Appl. No. 14/959,750, 13 pages.
Office Action, dated May 31, 2016, in connection with related U.S. Appl. No. 15/048,732, 12 pages.
Response, filed Aug. 31, 2016, to Office Action, dated May 31, 2016, in connection with related U.S. Appl. No. 15/048,732, 8 pages.
Final Office Action, dated Oct. 12, 2016, in connection with related U.S. Appl. No. 15/048,732, 15 pages.
Request for Continued Examination and Amendment, filed Jan. 10, 2017, responsive to the Final Office action, dated Oct. 12, 2016, in connection with related U.S. Appl. No. 15/048,732, 11 pages.
Supplemental Amendment and Response, filed Jan. 19, 2017, to Final Office Action, dated Oct. 12, 2016, in connection with related U.S. Appl. No. 15/048,732, 8 pages.
Office Action, dated Feb. 14, 2017, in connection with related U.S. Appl. No. 15/048,732, 15 pages.
International Search Report and Written Opinion, dated Dec. 17, 2014, in connection with related International Patent Application No. PCT/KR2014/007631, 8 pages.
International Preliminary Report on Patentability, dated Feb. 23, 2016, in connection with related International Patent Application No. PCT/KR2014/007631, 7 pages.

* cited by examiner

FIG. 3A                                    FIG. 3B

METHODS FOR TREATING THROMBOCYTOPENIA

CROSS-REFERENCE TO RELATED APPLICATIONS

This application is a continuation application of U.S. application Ser. No. 14/951,353, filed Nov. 24, 2015, which is a continuation application of International Application Serial No. PCT/US2015/031204, files May 15, 2015 which claims priority from U.S. Provisional 61/993,774, filed 15 May 2014 U.S. Provisional 61/993,784, filed 15 May 2014, U.S. Provisional 62/018,528 filed 27 Jun. 2014, U.S. Provisional 62/018,530 filed 27 Jun. 2014, U.S. Provisional 62/083,739 filed 24 Nov. 2014 and U.S. Provisional 62/083, 749 filed 24 Nov. 2014, the contents of each of which are incorporated herein by reference.

FIELD

The disclosure relates to methods for treating, controlling or mitigating leukopenia and/or thrombocytopenia, for example in the context of cancer chemotherapy, comprising administration of a monoacetyl-diacyl-glycerol compound, as well as compositions useful therefor.

BACKGROUND

During hematopoiesis, hematopoietic stem cells (HSCs) in bone marrow differentiate into common lymphocyte precursors (CLPs) and common myeloid precursors (CMPs). CMPs differentiate into cells of myeloid lineage, such as erythrocytes, megakaryocytes/platelets, neutrophils, eosinophils, basophils, monocytes, macrophages and dendritic cells. CLPs give rise to cells of lymphocyte lineage such as T cells, B cells and NK cells.

Functionally, blood cells comprise red blood cells, which supply oxygen to tissues, platelets, which control clotting, and leukocytes, which protect against infectious diseases and foreign substances. Leukocytes (white blood cells) include the white cells of the myeloid lineage such as neutrophils, eosinophils, basophils, and monocytes, as well as lymphocytes such as T-cells and B-cells. There are about 4,000-10,000 leukocytes per 1 µl of blood. The leukocyte population is generally made up of 50-60% neutrophils, 1-6% eosinophils, less than 1% basophils, 2-10% monocytes, and 20-30% lymphocytes. However, the level and composition of leukocytes can vary widely among individuals or in the same individual over time, depending on factors such as physical condition and inflammation status.

If the differentiation of HSCs into CMP cells is suppressed, the concentration of leukocytes in the blood will decrease below normal range, causing leukopenia. Leukopenia can be caused by bacterial or viral infection often. However, leukopenia can be also caused by aplastic anemia, leukemia, myelodysplastic syndrome (MDS) or other bone marrow disorders. While mild leukopenia will result in only minor deficiency in immune response, severe leukopenia can even cause sepsis.

As neutrophils are the most abundant leukocyte, leukopenia generally entails neutropenia. Neutrophils serve as the primary defense against infections by destroying bacteria in the blood. Patients with neutropenia are more susceptible to bacterial infections and are vulnerable to potentially lethal sepsis if the condition is not controlled. Absolute neutrophil count (ANC) varies by age and sex, with a normal range in adults of 1500 to 8000 cells per microliter (µl) of blood, although ANC in healthy adults is typically >2500 cells/µl. ANC<500 cells/µl is considered severe and is a very dangerous condition, correlating with a high risk of serious infection. Neutropenia may be caused by many things, e.g., cancer or other diseases that damage bone marrow, congenital disorders characterized by poor bone marrow function, viral infections that disrupt bone marrow function, autoimmune disorders that destroy neutrophils or bone marrow cells, overwhelming infections that use up neutrophils faster than they can be produced, or drugs that destroy neutrophils or damage bone marrow. Many anti-cancer drugs as well as radiation therapy for cancer may cause direct dose-dependent bone marrow suppression. Other anticancer drugs incite immune-mediated destruction of progenitor cells within the bone marrow compartment and in some cases increased destruction or clearance of peripheral neutrophils.

Various cytokines are involved in hematopoiesis. Granulocyte-colony stimulating factor (G-CSF or GCSF), also known as colony-stimulating factor 3 (CSF 3), is a glycoprotein that stimulates the hematopoietic precursor cells in the bone marrow to proliferate and differentiate into mature granulocytes and stem cells and release them into the bloodstream. It also induces release of hematapoietic stem cells (HSCs) from the bone marrow into the blood stream, although it does not specifically stimulate these cells. In humans, it exists in two active forms, the more abundant of which is 174 amino acids long; the other is 177 amino acids long. The pharmaceutical analogs of naturally occurring G-CSF are recombinant forms of the human 174-amino acid peptide (rhG-CSF), and include:

filgrastim (e.g. Neupogen® from Amgen), which made in *E. coli*, having the same activity, but differing from the natural glycoprotein in having an N-terminal methionine residue and lacking glycosylation;

lenograstim (e.g., Granocyte® from Chugai), which is made in mammalian cells (Chinese Hamster Ovary (CHO) cells), and so is essentially indistinguishable from human G-CSF;

pegfilgrastim, a PEGylated form of filgrastim, (e.g., Neulasta® from Amgen and Neulastim® from Roche), having a 20 kD monomethoxypolyethylene glycol moiety covalently bound to the N-terminal methionyl residue of filgrastim, which increases solubility and duration of action compared to filgrastim.

These drugs are approved in the US and many other countries to treat and mitigate neutropenia, primarily in cancer patients receiving chemotherapy, e.g., for one or more of the following indications to decrease the incidence of infection, as manifested by febrile neutropenia, in patients with non-myeloid malignancies receiving myelosuppressive anti-cancer drugs associated with a clinically significant incidence of febrile neutropenia;

to reduce the time to neutrophil recovery and the duration of fever, following induction or consolidation chemotherapy treatment of adults with acute myeloid lymphoma;

to reduce the duration of neutropenia and neutropenia-related clinical sequelae, e.g., febrile neutropenia in patients with nonmyeloid malignancies undergoing myeloablative chemotherapy followed by bone marrow transplantation;

to mobilize hematopoietic progenitor cells into the peripheral blood for collection by leukapheresis, which can then be transplanted into the patient following myeloablative chemotherapy, which may result in a decreased need for supportive care;

to reduce the incidence and duration of sequelae of neutropenia (eg, fever, infections, oropharyngeal ulcers) in symptomatic patients with congenital neutropenia, cyclic neutropenia, or idiopathic neutropenia Neupogen® is generally given at doses of 4 to 8 mcg/kg/day, up to 10 mcg/kg/day. Higher doses, up to 138 mcg/kg/day have been administered without toxic effects, but there is a flattening of the dose response curve above daily doses of greater than 10 mcg/kg/day. Side effects of Neupogen® and other forms of G-CSF may include mild-to-moderate bone pain after repeated administration, local skin reactions at the site of injection, allergic reactions, enlarged or ruptured spleen, alveolar hemorrhage, acute respiratory distress syndrome (ARDS), hemoptysis, and (in patients with pre-existing sickle cell disorders) sickle cell crises. G-CSF drugs are generally not given in patients with chronic myelogenous leukemia (CML) or myelodysplastic syndrome, as they could potentially spur the growth of cancer cells.

Platelets, also called thrombocytes, are colorless blood cells that help the blood to clot. Normal human platelet counts range from 130,000-400,000 platelets per microliter (µl) of blood. As in the case of neutropenia, if the differentiation of HSCs into CMPs is suppressed, or if platelets are destroyed, for example as a result of an autoimmune condition, the concentration of platelets in the blood may drop below normal ranges (thrombocytopenia). A platelet count of <50,000 platelets/µl of blood is considered a serious condition, and with a count of <20,000 platelets/µl of blood, life-threatening internal bleeding can occur spontaneously. Thrombocytopenia has few symptoms until the platelet count is extremely low, when impairment to clotting is evidenced by spontaneous bruising, bruising after very mild trauma, petechia (red or purple spots on the skin caused by tiny hemorrhages in the skin and mucous membranes), and excessive bleeding from minor cuts, nosebleeds or brushing the teeth. Other symptoms may include malaise, fatigue and general weakness (with or without accompanying blood loss). Thrombocytopenia may be caused by, e.g., bacterial or viral infection, cirrhosis, chemotherapy or radiation therapy, acute leukemia, aplastic anemia, or autoimmune conditions, or may be a side effect of various medications. Like neutropenia, thrombocytopenia is a frequent side effect of chemotherapy or radiation therapy for cancer.

Thrombocytopenia may cause, exacerbate or be co-morbid with anemia. Anemia may be caused by active bleeding, for example from heavy menstrual bleeding, wounds, gastrointestinal ulcers, or cancers such as cancer of the colon which may slowly ooze blood, and such bleeding may be caused or exacerbated by thrombocytopenia. Anemia is also common in patients suffering from chronic disease, poor nutrition, and kidney failure, all of which may occur in cancer patients receiving chemotherapy or radiation therapy.

Multiple myeloma (MM) is a cancer of the plasma cells, which produce antibodies. Myeloma prevents the normal production of antibodies, leaving the immune system weakened and the patient susceptible to infection, while producing defective antibodies that may cause kidney damage. The multiplication of myeloma cells also interferes with the normal production and function of red and white blood cells, and the myeloma cells commonly produce substances that cause bone destruction, leading to bone pain and/or fractures. Multiple myeloma is specifically stimulated by G-CSF. Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults. The myelodysplastic syndromes (also known as MDS or myelodysplasia) are characterized by ineffective production (or dysplasia) of the myeloid class of blood cells. Patients with MDS can develop severe anemia and require blood transfusions. In some cases, the disease worsens and the patient develops cytopenias caused by progressive bone marrow failure. Chronic myelogenous leukemia (CML) is a form of leukemia characterized by the increased and unregulated growth of predominantly myeloid cells in the bone marrow and the accumulation of these cells in the blood. CML is a clonal bone marrow stem cell disorder in which a proliferation of mature granulocytes (neutrophils, eosinophils and basophils) and their precursors is found.

Bone marrow malignancies, such as MM, AML, MDS and CML, may be induced or stimulated by granulocyte-colony stimulating factor (G-CSF). While in a few cases, G-CSF has been deliberately used to stimulate cancer cell proliferation in these types of cancers, in order to enhance their susceptibility to chemotherapeutic agents (which generally target proliferating cells), recombinant G-CSF drugs (e.g., filgrastim, lenograstim, or pegfilgrastim) are not generally a good option to treat chemotherapy-induced neutropenia in patients recovering from these types of cancers.

For example, lenalidomide (Revlimid®) is a derivative of thalidomide, used to treat multiple myeloma, myelodysplastic syndromes and other cancers. Lenalidomide has significantly improved overall survival in myeloma (which generally has a poor prognosis), but the drug is quite toxic. Myelosuppression leading to severe neutropenia and thrombocytopenia, is the major dose limiting toxicity.

New approaches to treatment and management of neutropenia and thrombocytopenia are needed, for example to permit more aggressive chemotherapy at higher doses and/or for longer duration than is currently safe, and particularly in patients having G-CSF-inducible cancers, whose neutropenia cannot be managed with G-CSF.

Deer antler is a traditional Asian medicine, prepared by drying uncornified antler of a deer. Deer antler has been acclaimed to have various medical effects, such as growth- and development-promoting effects, promoting hematopoietic function, treating nervous breakdown, beneficial to cardiac insufficiency, improving the function of five viscera and six entrails, as described in the Dong-eui Bogam, a Korean medical book first published in 1613. It has been reported that certain components of deer antler, including rac-1-palmitoyl-2-linoleoyl-3-acetylglycerol (PLAG) obtained from chloroform extracts of the deer antler, have growth-stimulating activities of hematopoietic stem cells and megakaryocytes (WO 99/26640). It is also reported that monoacetyldiacylglycerol derivatives which are active components of the deer antlers are effective in treating autoimmune diseases, sepsis, cancers such as bile duct cancer, kidney cancer or malignant melanoma, and so on (WO 2005/112912).

BRIEF SUMMARY OF THE INVENTION

The monoacetyldiacylglycerols described herein, particularly PLAG, have surprisingly been found to stimulate neutrophil production by a mechanism different from G-CSF, to enhance platelet production, and to reduce neutrophil migration out of the blood. These compounds are therefore useful to help treat and mitigate neutropenia and/or thrombocytopenia, for example when caused by chemotherapeutic agents such as lenalidomide, particularly in patients suffering from cancers which can be induced or exacerbated by G-CSF. The monoacetyldiacylglycerols described herein, particularly PLAG, moreover help prevent the metastasis of blood cancers like these by reducing the migration of cancerous cells from the blood to the lymph nodes. The monoacetyldiacylglycerols described herein also reduce complement activity, and so are useful to protect against complement-mediated depletion of platelets, for example caused by an autoimmune condition.

The present disclosure shows that the monoacetyldiacylglycerol of Formula 1 described herein, particularly, PLAG of Formula 2, is effective for the prevention and treatment of thrombocytopenia and leukopenia, e.g., neutropenia, by enhancing differentiation and propagation of HSC into CMP and suppressing the activity of Complement:

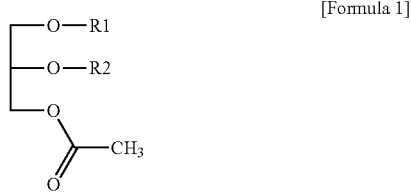

[Formula 1]

wherein $R_1$ and $R_2$ are independently a fatty acid residue of 14 to 22 carbon atoms, for example:

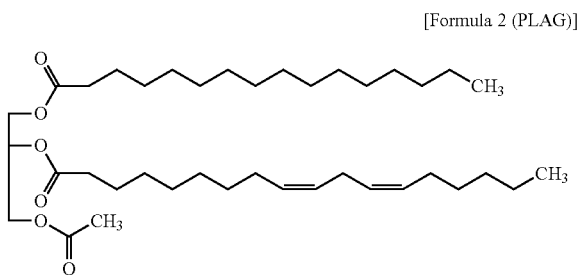 [SMILES: CCCCC/C=C\C/C=C\CCCCCCCC(=O)OC(COC(C)=O)COC(=O)CCCCCCCCCCCCCCC]

[Formula 2 (PLAG)]

In some embodiments, the present disclosure provides methods for treating, (e.g. inhibiting, reducing, controlling, mitigating, or reversing) a condition selected from leukopenia (e.g. neutropenia), and/or thrombocytopenia, comprising administering to a patient in need thereof an effective amount of a compound of formula 1, e.g., PLAG, to a patient in need thereof.

In some embodiments, the present disclosure provides methods for preventing or suppressing upregulated or activated Complement 3 (C3), comprising administering of an effective amount of a compound of formula 1, e.g., PLAG, to a subject in need thereof.

In some embodiments, the present disclosure provides methods for treating, controlling or mitigating leukopenia and enhancing the innate immunity, comprising administering of an effective amount of a compound of formula 1, e.g., PLAG, to a subject in need thereof by increasing the ratio of the white cells of the myeloid lineage such as neutrophils, eosinophils, monocytes and, at the same time, reducing the lymphocytes, which are immunocytes.

In some embodiments, the present disclosure provides methods of treating cancer comprising administering to a patient in need thereof a chemotherapeutic agent, in conjunction with a neutrophil- or platelet-protective amount of a compound of formula 1, e.g. PLAG, wherein the chemotherapeutic agent is administered at a dosage and/or for a period of time which would cause neutropenia and/or thrombocytopenia in the patient are the patient not receiving the compound of formula 1.

The present disclosure provides, in some embodiments, methods for treating, controlling or mitigating neutropenia and/or thrombocytopenia in patients receiving a chemotherapeutic agent, for example, lenalidomide, to treat a cancer which is stimulated by G-CSF (e.g., multiple myeloma, acute myeloid leukemia, chronic myelogenous leukemia or myelodysplastic syndrome), the method comprising administering of an effective amount of a compound of formula 1, e.g. PLAG, to a patient in need thereof.

In some embodiments, the disclosure provides methods of treating a blood cancer, e.g., selected from (e.g., multiple myeloma, acute myeloid leukemia, chronic myelogenous leukemia or myelodysplastic syndrome), for example a blood cancer which may be induced or exacerbated by G-CSF, comprising co-administering (sequentially or simultaneously) a chemotherapeutic agent, e.g., lenalidomide, and a compound of formula 1.

In some embodiments the disclosure provides a method for treatment (including prophylaxis) of neutropenia and/or for mobilizing peripheral blood progenitor cells (PBPCs), comprising administering (sequentially or simultaneously) an effective amount of (i) a compound of Formula 1, e.g. PLAG, and (ii) a G-CSF, e.g., selected from filgrastim, pegfilgrastim, and lenograstim, to a patient in need thereof.

In some embodiments the disclosure provides a method to mitigate or treat side effects of G-CSF, e.g., thrombocytopenia and/or bone pain induced by G-CSF, comprising co-administering, sequentially or simultaneously, a compound of formula 1, e.g., PLAG, to a patient in need thereof.

In another embodiment, the disclosure provides a method of treating anemia comprising administering an effective amount of a compound of formula 1, especially PLAG, to a patient in need thereof. Because the compounds of formula 1 promote the differentiation of HSCs to CMPs, thus expanding cells of myeloid lineage, they are useful to enhance production of erythrocytes, and at the same time, by enhancing platelet numbers, they reduce chronic bleeding, for example from stomach ulcers or excessive menstrual flow, due to low platelet counts, thereby both enhancing and preserving erythrocytes and reducing anemia.

In addition, the present disclosure provides a pharmaceutical composition, including a functional health food, comprising a compound of formula 1, for preventing or improving of leukopenia or thrombocytopenia.

The disclosure further provides the compounds of formula 1, and pharmaceutical compositions comprising compositions of formula 1, for use in methods as described, and for use in the manufacture of medicaments for use in in methods as described.

In one embodiment, the disclosure provides a novel pharmaceutical unit dose drug product, in the form of a soft gelatin capsule for oral administration containing 250-1000 mg, e.g., 500 mg, of PLAG drug substance, substantially free of other triglycerides, together with 0.1-3 mg, e.g. 1 mg of a pharmaceutically acceptable tocopherol compound, e.g., α-tocopherol, as an antioxidant, e.g., for administration once or twice a day, at a daily dosage of 500 mg to 4,000 mg.

Further areas of applicability of the present invention will become apparent from the detailed description and examples provided hereinafter. It should be understood that the detailed description and specific examples, while indicating certain preferred embodiments of the invention, are intended for purposes of illustration only and are not intended to limit the scope of the invention.

BRIEF DESCRIPTION OF DRAWINGS

FIG. 3A confirms that PLAG does not affect the cellular propagation and death in the WST-1 assay in a HepG2 cell line. FIG. 3B shows that expression of C3 is decreased dose-dependently by the administration of PLAG.

DETAILED DESCRIPTION OF THE INVENTION

Figure 1:
FIG. 1 depicts a reporter assay for STAT1 and STAT6 transcriptional activity in PLAG-treated HepG2 cells.

Compositions of the present disclosure for treating thrombocytopenia and/or leukopenia include glycerol derivatives having one acetyl group and two acyl groups of the following Formula 1:

[Formula 1]

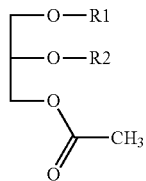

wherein R1 and R2 are independently a fatty acid residue of 14 to 22 carbon atoms.

In the present disclosure, the glycerol derivatives of Formula 1 are sometimes referred as monoacetyldiacylglycerols (MDAG). Fatty acid residue refers to the acyl moiety resulting from formation of an ester bond by reaction of a fatty acid and an alcohol. Non-limiting examples of $R_1$ and $R_2$ thus include palmitoyl, oleoyl, linoleoyl, linolenoyl, stearoyl, myristoyl, arachidonoyl, and so on. Preferable combinations of $R_1$ and $R_2$ ($R_1/R_2$) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyldiacylglycerol derivatives of Formula 1 can be (R)-form, (S)-form or a racemic mixture, and may include their stereoisomers. Where the $R_1$ and/or $R_2$ substituents are unsaturated fatty acid residues, the double bond(s) may have the cis configuration.

In one embodiment, the monoacetyldiacylglycerol is a compound of the following Formula 2:

[Formula 2]

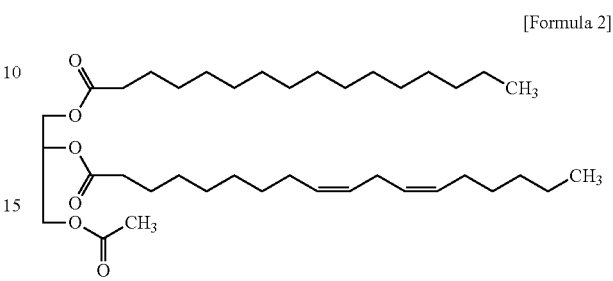

The compound of Formula 2 is 1-palmitoyl-2-linoleoyl-3-acetylglycerol, sometimes referred as "PLAG" in this specification. $R_1$ and $R_2$ of the compound of Formula 2 are palmitoyl and linoleoyl, respectively. The 2-carbon on the glycerol moiety is chiral. PLAG is generally provided as the racemate, and the R- and S-enantiomers appear to have the same activity. It is known that PLAG of Formula 2 increases survivability ratio of animals in sepsis animal model experiment using cecal-ligation-puncture, and shows no toxicity in a GLP (Good Laboratory Practice) toxicity test. However, the effect of the monoacetyldiacylglycerol compounds including PLAG on thrombocytopenia and leukopenia, especially on neutropenia and the effect of the monoacetyldiacylglycerol compound in combination with G-CSF drugs are not known or disclosed in the prior arts.

The monoacetyldiacylglycerol compounds can be separated and extracted from the natural deer antler or can be produced by conventional organic synthesis methods. More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method is further fractionated and purified using series of silica gel column chromatograph and TLC method to obtain the monoacetyldiacylglycerol compound for the present invention. A solvent for the extraction is selected among chloroform/methanol, hexane/ethylacetate/acetic acid, but not limited thereto.

A chemical synthetic method for the preparation of monoacetyldiacylglycerol compounds is shown, for example, in Korean Registered Patents No. 10-0789323 and No. 10-1278874, the contents of which are incorporated herein by reference. For example, PLAG can be synthesized by acylating the hydroxy groups of glycerin with acetyl, palmitoyl and linoleoyl functional groups. The final product is similar to the natural component identified and isolated from deer antlers. Both are racemates.

In the present invention, the term "treatment" or "treating" encompasses prophylaxis, reduction, amelioration or elimination of the condition to be treated, for example suppression or delay of onset of thrombocytopenia and leukopenia by the administration of the pharmaceutical composition of the present disclosure (sometimes referred to as prevention), as well as improving thrombocytopenia and leukopenia or changing symptoms of thrombocytopenia and leukopenia to more beneficial states.

In vitro pharmacology studies in cell lines show that PLAG is capable of inhibiting the PKCθ/p38/ERK pathway, which is involved in the maturation of lymphoid progenitor cells from HSC. Also, in vitro induction of increased colony formation is shown in bone marrow-derived HSC. Moreover, PLAG inhibits complement C3 expression in human HMC-1 cells. In vivo PLAG is shown to increase nodule formation in spleens of irradiated mice transplanted with syngeneic HSC. PLAG administration prevents cytotoxic agent-induced neutropenia and improves the survival rate in tamoxifen-treated mice.

The monoacetyldiacylglycerol compounds, especially PLAG, promote differentiation of hematopoietic stem cell (HSC) to common myeloid precursor (CMP), which is a precursor of (i) megakaryocytes which differentiate into platelets and (ii) myeoloblasts which differentiate into neutrophil, eosinophil, basophil, monocyte, etc., rather than to common lymphocyte precursor (CLP), thus increasing the ratio of macrophages, such as neutrophils, eosinophils, monocytes, etc., and reducing the excessively produced lymphocytes. They prevent and treat leukopenia, and more specifically prevent, reduce or treat neutropenia to enhance the innate immunity.

In addition to increasing colony formation and activating differentiation of HSCs to myeloid cells such as neutrophils and megakaryocyte), the monoacetyldiacylglycerol compounds, especially PLAG, reduce complement activation. Published reports on the role of a complement-dependent mechanism in drug-induced neutropenia and the role of neutrophils in vascular inflammation and the response to sepsis suggest that complement activation may be involved in the thrombocytopenia and leukopenia induced by chemotherapy. Without being bound to any theory, it is believed that the compounds suppress C3 by inhibiting the activity of STAT6, which may be up-regulated or activated by chemotherapy. A STAT6 inhibitor would block the STAT6 signal transduction in the cell by IL-4, which in turn would suppress expression of C3.

Selective reduction of complement activity using the monoacetyldiacylglycerol compounds of formula 1, especially PLAG, thus contributes to their effectiveness against chemotherapy-induced neutropenia and thrombocytopenia. The reduction of complement activity additionally enhances treatment of neutropenia by reducing complement-induced exit of neutrophils from circulation. It also enhances treatment of thrombocytopenia by reducing complement-mediated destruction of platelets, for example in autoimmune thrombocytopenia.

The monoacetyldiacylglycerol compounds of formula 1, particularly PLAG, stimulate neutrophil production by a mechanism different from G-CSF and so can enhance the effects of G-CSF drugs such as filgrastim, pegfilgrastim, and lenograstim in treating or mitigating neutropenia and/or mobilizing peripheral blood progenitor cells (PBPCs) to a degree not achievable by administering G-CSF alone. The monoacetyldiacylglycerol compound may also in some cases mitigate the side effects of G-CSF, e.g., by enhancing platelet production and by reducing the bone pain associated with G-CSF administration. Accordingly, the disclosure provides a method for treating neutropenia and/or mobilizing PBPCs, comprising administration of a monoacetyldiacylglycerol, e.g., PLAG, to a patient in need thereof, simultaneously, sequentially or in combination with a granulocyte colony stimulating factor (G-CSF). The patient may, for example, be a cancer patient receiving chemotherapy and/or radiation therapy, or other patient suffering from or at risk of neutropenia, and the monoacetyldiacylglycerol, e.g., PLAG, may be given during and/or after the chemotherapy and/or radiation treatment, to treat the resulting neutropenia, and/or may be given before, to help mitigate the effects of such treatment, or to mobilize hematopoietic progenitor cells into the peripheral blood for collection by leukapheresis, and subsequent use to rescue the patient following myeloablative chemotherapy.

The monoacetyldiacylglycerols of formula 1, particularly PLAG, stimulate neutrophil production by a mechanism different from G-CSF. Because the compounds of formula 1, e.g., PLAG, enhance platelet levels as well as neutrophil levels, it may be hypothesized that they promote proliferation and differentiation upstream from G-CSF. Moreover, the compounds of formula 1, e.g., PLAG, reduce complement activation, reduce exit of neutrophils into the lymph nodes following inflammatory stimulation, and reduce destruction of platelets, all of which re activities different from G-CSF.

Thus the compounds of formula 1, particularly PLAG, can help mitigate neutropenia and thrombocytopenia, caused by chemotherapeutic agents such as lenalidomide, particularly in patients who cannot use G-CSF, for example patients suffering from cancers which can be induced or exacerbated by G-CSF. As the compounds of formula 1, particularly PLAG, do not compete with G-CSF but rather enhance the effects of G-CSF, they may be used in combination with G-CSF to provide a level of efficacy that is not attainable with G-CSF alone, or to reduce the level of G-CSF necessary for efficacy, e.g., in patients experiencing side effects frm G-CSF The compounds of formula 1, particularly PLAG, moreover help prevent the metastasis of blood cancers like these by reducing the migration of cancerous cells from the blood to the lymph nodes. As described in the examples, when mice are injected with lipopolysaccharide (LPS) to provoke an immune response, in the presence or absence of PLAG, in the mice treated with LPS and PLAG, the concentration of neutrophils is increased, whereas neutrophil levels in the lymph are lower, compared with the control of LPS only. This shows that while PLAG enhances neutrophil levels in the blood, it also inhibits migration to the lymph node.

Pharmaceutical composition comprising monoacetyldiacylglycerols may consist of only or substantially pure monoacetyldiacylglycerol derivatives of Formula 1, or may include active components (monoacetyldiacylglycerol derivatives of Formula 1) and conventional pharmaceutically acceptable carriers, excipients, or diluents. The amount of monoacetyldiacylglycerol in the pharmaceutical composition can be widely varied without specific limitation, and is specifically 0.0001 to 100 weight %, e.g., 0.001 to 50 weight %, 0.01 to 20 weight %, or 95-99 weight % with respect to the total amount of the composition. The pharmaceutical composition may be formulated into solid, liquid, gel or suspension form for oral or non-oral administration, for example, tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various excipients such as wetting agent, sweeting agent, flavoring agent, and preserving agent. The formulation for non-oral administration includes sterilized aqueous solution, non-aqueous solution, freeze-dried formulation, suppository, and so on, and solvent for such solution may include propylene glycol, polyethylene glycol, vegetable oil such as olive oil, and ester for syringe injection such as ethyl oleate. Base materials of the suppository may include witepsol, macrogol, tween 61, cacao butter, Laurin and glycerogelatine.

The monoacetyldiacylglycerol compound can be administered in a pharmaceutically effective amount. The term "pharmaceutically effective amount" is used to refer to an amount that is sufficient to achieve a desired result in a medical treatment. The "pharmaceutically effective amount" can be determined according to the subject's category, age, sex, severity and type of disease, activity of drug, sensitivity to drug, administration time, administration route, excretion rate, and so forth.

The term "treatment" or "treating" includes prophylaxis, mitigation, amelioration, delay or reduction of symptoms, as well as partial or complete elimination or prevention of symptoms, of thrombocytopenia and/or leukopenia by administering the composition of the present invention. The composition of the present disclosure can be administered alone or with other medicines sequentially or simultaneously. When the composition of the present disclosure is administered with the G-CSF drug, the term "treatment" or "treating" includes prophylaxis, mitigation, amelioration, delay or reduction of symptoms, as well as partial or complete elimination or prevention of symptoms, of neutropenia and/or side effects of G-CSF, by administering the monoacetyldiacylglycerol in combination (sequentially or simultaneously) with the G-CSF drug.

The preferable amount of the composition of the present disclosure can be varied according to the condition and weight of patient, severity of disease, formulation type of drug, administration route and period of treatment. An appropriate total amount of administration per 1 day can be determined by a physician, and is generally about 0.05 to 200 mg/kg. Extrapolating from in vivo experiments in animals and in vitro experiments in cells, the preferable total administration amount per day is determined to be 0.1 to 100 mg/kg for an adult human. For example, the total amount of 50 mg/kg can be administered once a day or can be administered in divided doses twice, three, or four times daily.

For example, in one embodiment, the disclosure provides a novel pharmaceutical composition in unit dose form, in the form of a soft gelatin capsule for oral administration containing 250-1000 mg, e.g., 500 mg, of PLAG drug substance, free of other triglycerides, together with 0.1-3 mg, e.g. 1 mg of a pharmaceutically acceptable tocopherol compound, e.g., α-tocopherol, as an antioxidant, e.g., for administration once or twice a day, at a daily dosage of 500 mg to 4,000 mg, for example 1000 mg/day administered as a divided dose 500 mg in the morning and 500 mg in the evening.

The composition of the present disclosure can be administered to any subject that requires the prevention or treatment of thrombocytopenia and leukopenia. For example, the composition of the present disclosure can be administered to not only human but also non-human animal (specifically mammals) such as monkey, dog, cat, rabbit, guinea pig, rat, mouse, cow, sheep, pig, goat, and so on. The composition of the present disclosure can be administered by conventional various methods, for example, by oral or rectum administration, or by intravenous (i.v.), intramuscular (i.m.), subcutaneous (s.c.) or cerebrovascular injection. As monoacetyl-diacylglycerols are orally active, they are generally administered orally, for example in the form of a gelatin capsule, or in the form of a health functional food, that is, a food which contains an effective amount of monoacetyldiacylglycerol of formula 1.

The disclosure thus provide, in one aspect, a method (Method 1) for treating, (e.g. inhibiting, reducing, controlling, mitigating, or reversing) a condition selected from leukopenia (e.g. neutropenia), and/or thrombocytopenia, comprising administering to a patient in need thereof an effective amount (e.g. a neutrophil- or platelet-protective amount) of a compound of Formula 1:

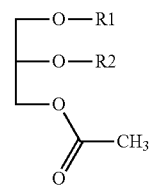

wherein $R_1$ and $R_2$ are independently a fatty acid group of 14 to 22 carbon atoms, e.g., PLAG;
for example,
1.1. Method 1 wherein $R_1$ and $R_2$ are independently selected from the group consisting of palmitoyl, oleoyl, linoleoyl, linolenoyl, stearoyl, myristoyl, and arachidonoyl.
1.2. Method 1 or 1.1 wherein R1 and R2 (R1/R2) is selected from the group consisting of oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl.
1.3. Any foregoing method wherein the Compound of Formula 1 is a compound of Formula 2 (PLAG):

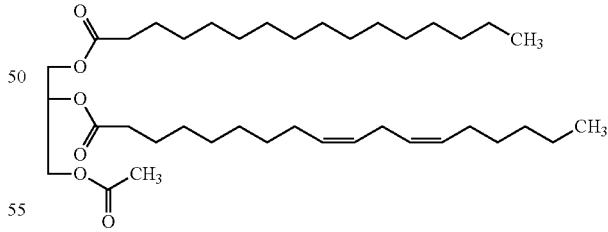

1.4. Any foregoing method wherein the compound of Formula 2 is administered in a pharmaceutical composition which is substantially free of other monoacetyldiacylglycerols, e.g, wherein at least 95%, for example at least 99% of the total monoacetyldiacylglycerols in the formulation are of Formula 2.
1.5. Any foregoing method wherein the compound of Formula 2 is administered in a pharmaceutical composition which is substantially free of other monoacetyl diacyl glycerol compounds.

1.6. Any foregoing method wherein the compound of Formula 2 is administered in a pharmaceutical composition which is substantially free of other triglyceride compounds.
1.7. Any foregoing method wherein the Compound of Formula 1 is separated and extracted from natural deer antler.
1.8. Any foregoing method wherein the compound of Formula 1 is produced by chemical synthesis.
1.9. Any foregoing method wherein the compound of Formula 1 is administered in the form of a pharmaceutical composition for oral administration.
1.10. Any foregoing method wherein the compound of Formula 1 is administered in the form of a pharmaceutical composition which is a soft gelatin capsule containing the Compound of Formula 1 in combination or association with a pharmaceutically acceptable diluent or carrier, for example wherein the pharmaceutically acceptable diluent or carrier comprises an edible oil, e.g., a vegetable oil, for example olive oil.
1.11. Any foregoing method wherein the compound of Formula 1 is administered in the form of a pharmaceutical composition comprising 0.0001 to 100.0 weight %, for example 50-95%, or 95-99%, by weight of the composition.
1.12. Any foregoing method wherein the composition further comprises a pharmaceutically acceptable antioxidant, for example ascorbic acid (AA, E300) and tocopherols (E306), as well as synthetic antioxidants such as propyl gallate (PG, E310), tertiary butylhydroquinone (TBHQ), butylated hydroxyanisole (BHA, E320) and butylated hydroxytoluene (BHT, E321), for example α-tocopherol.
1.13. Any foregoing method wherein the compound of Formula 1 is a compound of Formula 2 administered in the form of a soft gelatin capsule containing 250 mg of the Compound of Formula 2 in combination or association with approximately 50 mg of a pharmaceutically acceptable diluent or carrier, for example an edible oil, e.g., a vegetable oil, e.g., olive oil.
1.14. Any foregoing method wherein the Compound of Formula 1 is administered in the form of a functional food, for example as an additive or admixture to a food suitable for human consumption.
1.15. Any foregoing method wherein the Compound of Formula 1 is administered once a day (q.d.) or twice a day (b.i.d.).
1.16. Any foregoing method wherein the total daily dosage of the Compound of Formula 1 250 mg to 2000 mg/day, for example 500 mg-1500 mg/day, e.g., 500 mg/day, 1000 mg/day, or 1500 mg/day.
1.17. Any foregoing method wherein the Compound of Formula 1 is administered in a dosage of 500 mg twice a day, e.g., morning and evening.
1.18. Any foregoing method wherein the Compound of Formula 1 is administered in a dosage of 500 mg once a day, e.g., in the evening.
1.19. Any of the foregoing methods wherein the Compound of Formula 1 is administered over a period of at least two weeks, e.g., at least a month.
1.20. Any foregoing method wherein the pharmaceutical composition may be formulated into solid, liquid, gel or suspension form for oral or non-oral administration.
1.21. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.
1.22. Any foregoing method wherein the condition to be treated is neutropenia.
1.23. Any foregoing method wherein the condition to be treated is caused by one of the disease selected from the group consisting of pneumonia, ear infection, oral gum infection, arsenic poisoning, hemodialysis, chemical compound, protein, anticancer agent, chemotherapy and irradiation therapy.
1.24. Any foregoing method wherein the condition to be treated is caused by one of the disease selected from the group consisting of pneumonia, ear infection, oral gum infection, arsenic poisoning, hemodialysis, chemical compound, protein, anticancer agent, chemotherapy and irradiation therapy.
1.25. Any foregoing method wherein the condition to be treated is caused or exacerbated by a compound selected from the group consisting of ziv-aflibercept, brentuximab vedotin, pralatrexate, ganciclovir, valganciclovir, romidepsin, ruxolitinib, decitabine, imatinib, topotecan, lenalidomide, irinotecan, interferons, phenylhydrazine, tamoxifen, lipopolysaccharide, anthracyclin antibiotics, gemcitabine, cytoxan, paclitaxel, alkylating antineoplastic agent, DNA intercalating agent, topoisomerase inhibitor, and derivatives or mixtures thereof.
1.26. Any foregoing method wherein the condition to be treated includes thrombocytopenia induced by a drug, e.g., a drug selected from Ziv-aflibercept, Brentuximab vedotin, Pralatrexate, Ganciclovir, Valganciclovir, Romidepsin, Ruxolitinib, Decitabine, Imatinib, Topotecan, Lenalidomide, Irinotecan, Interferons, Phenylhydrazine, Tamoxifen, Lipopolysaccharide, Anthracyclin antibiotics (e.g. daunorubicin, doxorubicin (=Adriamycin)), Gemcitabine, Cytoxan, Paclitaxel, Alkylating antineoplastic agent, DNA intercalating agent (e.g. alkylating agent, bendamustin, mustard), Topoisomerase inhibitor, Bortezomib, Temsirolimus, Vorinostat, Ifosfamide, Lxabepilone and their derivatives.
1.27. Any foregoing method wherein the condition to be treated includes leukopenia, e.g., neutropenia, induced by a drug, e.g., a drug selected from Ziv-aflibercept, Brentuximab Vedotin, Deferiprone, Gemcitabine, Pralatrexate, Ganciclovir, Valganciclovir, Thalidomide, Romidepsin, Boceprevir, Decitabine, Imatinib, Topotecan, Lenalidomide, Paclitaxel, Olanzapine, Irinotecan, Paliperidone, Interferons, Lipopolysaccharide, tamoxifen, Flecainide (a class 1C cardiac antiarrhythmic drug), Phenytoin, Indomethacin, Propylthiouracil, Carbimazole, Chlorpromazine, Trimethoprim/sulfamethoxazole (cotrimoxazole), Clozapine, Ticlodipine, and their derivatives, Cyclophosphamide, Mechlorethanime, Chlorambucil, Melphalan, Carmustine (BCNU), Lomustine (CCNU), Procarbazine, Dacarbazine (DTIC), Altretamine, Cisplatin, Carboplatin, Actinomycin D, Etoposide, Topotecan, Irinotecan, Doxorubicin & daunorubicin, 6-Mercaptopurine, 6-Thioguanine, Idarubicin, Epirubicin, Mitoxantrone, Azathioprine, 2-Chloro deoxyadenosine, Hydroxyurea, Methotrexate, 5-Fluorouracil, Cytosine arabinoside, Azacytidine, Gemcitabine, Fludarabine phosphate, Vincristine, Vinblastine, Vinorelbine, Paclitaxel, Docetaxel, Tamoxifen, Pemetrexed, Nab-paclitaxel, Dasatinib, Paralatrexate, Decitabine, Romidepsin, Imatinib, Lenalidomide, Sunitinib, Oxaliplatin, and Thalidomide 1.28. Any foregoing method wherein the patient receives or is intending to receive chemotherapy at a dose sufficient to cause neutropenia or thrombocytopenia in the absence of treatment with a compound of formula 1, or is suffering from neutropenia or thrombocytopenia consequent to chemotherapy.

1.29. Any of the foregoing methods wherein the patient is a cancer patient receiving myelosuppressive chemotherapy.

1.30. Any of the foregoing methods wherein the patient is a cancer patient receiving myelosuppressive chemotherapy, wherein the treatment with the compound of Formula 1 is suspended for a period at least 24 hours prior until at least 24 hours after the administration of the chemotherapy, e.g., to reduce the vulnerability of cells stimulated by the compound of Formula 1 to the chemotherapy.

1.31. Any of the foregoing methods wherein the patient is a cancer patient receiving a bone marrow transplant.

1.32. Any of the foregoing methods wherein the patient is a cancer patient, the compound of formula 1 is administered prior to myeloablative chemotherapy, to enhance levels of peripheral blood progenitor cells, which are collected for reintroduction to the patient subsequent to myeloablative chemotherapy, and optionally, the compound of formula 1 is also administered subsequently to myeloablative chemotherapy.

1.33. Any foregoing method wherein the patient suffers from chronic neutropenia, e.g., congenital neutropenia, cyclic neutropenia or idiopathic neutropenia.

1.34. Any of the foregoing methods wherein the condition to be treated includes neutropenia, e.g., wherein "neutropenia" is considered to be a count of 2000 or fewer, e.g., 1,700 or fewer, e.g. 1500 Or fewer neutrophils per microliter of blood.

1.35. Any of the foregoing methods wherein treatment is continued until the patient has at least 5000, e.g., at least 8000, e.g. at least 10,000 neutrophils per microliter of blood.

1.36. Any of the foregoing methods wherein the neutropenia is associated with fever.

1.37. Any of the foregoing methods wherein the Compound of Formula 1 is administered in an amount effective to mitigate or treat side effects of G-CSF, e.g., thrombocytopenia and/or bone pain induced by G-CSF.

1.38. Any of the foregoing methods wherein the patient suffers from or is at risk of neutropenia or thrombocytopenia due to treatment with one or more chemotherapeutic agents selected from cyclophosphamide, doxorubicin, etoposide, ifosfamide, mesna, cisplatin, gemcitabine, and tamoxifen.

1.39. Any of the foregoing methods wherein the patient suffers from or is at risk of neutropenia or thrombocytopenia due to radiation therapy.

1.40. The method of any preceding claim wherein the condition to be treated is caused in whole or in part by chemotherapy.

1.41. The method of any preceding claim wherein the condition to be treated is caused in whole or in part by radiation therapy.

1.42. Any foregoing method wherein the condition to be treated includes thrombocytopenia, e.g. wherein thrombocytopenia is considered to be less than 130,000, e.g., less than 100,000, e.g., less than 50,000 platelets per microliter (µl) of blood.

1.43. Any foregoing method wherein the patient suffers from chronic thrombocytopenia, e.g., due to cancer, viral infection, aplastic anemia, immune thrombocytic purpura (ITP), thrombotic thrombocytopenic purpura (TTP) or liver disease.

1.44. Any foregoing method wherein the condition treated is thrombocytopenia caused by or coincident with a condition selected from the group consisting of petechiae, stomach bleeding, hematuria (bleeding in urine), excessive menstrual flow, stroke, blindness, idiopathic thrombocytopenic purpura (ITP), hyper-spleen activities, cirrhosis, hepatitis (especially hepatitis C), chronic liver disease, leukemia, lymphoma, lupus, human immunodeficiency virus (HIV) infection, a chemical compound, an anticancer agent, a protein, and irradiation therapy.

1.45. Any of the foregoing methods wherein treatment is continued until the patient has at least 50,000, e.g., at least 100,000, e.g. at least 130,000 platelets per microliter of blood.

1.46. Any of the foregoing methods wherein the condition treated is neutropenia and the patient receives a chemotherapeutic agent for treatment of a cancer which may be induced or stimulated by G-CSF, for example wherein the chemotherapeutic agent is selected from one or more of cyclophosphamide, doxorubicin, etoposide, ifosfamide, mesna, cisplatin, gemcitabine, tamoxifen and lenalidomide; for example wherein the chemotherapeutic agent is lenalidomide; for example wherein the cancer is multiple myeloma, chronic myelogenous leukemia (CML), acute myeloid leukemia, or myelodysplastic syndrome.

1.47. Any foregoing method wherein the compound of formula 1 is administered prior to myeloablative chemotherapy to enhance levels of peripheral blood progenitor cells which are collected for reintroduction to the patient subsequent to myeloablative chemotherapy, and optionally, the compound of formula 1 is also administered subsequently to myeloablative chemotherapy.

1.48. Any foregoing method wherein the compound of formula 1 induces differentiation of hematopoietic stem cell (HSC) to form common myeloid precursor (CMP), neutrophil, eosinophil and monocyte, and suppresses differentiation of hematopoietic stem cell (HSC) to form common lymphoid precursor (CLP) formation of common lymphocyte precursor and lymphocytes.

1.49. Any foregoing method wherein the condition to be treated is both neutropenia and thrombocytopenia.

1.50. Any foregoing method wherein the treatment is prophylactic.

1.51. Any foregoing method wherein the patient is a human.

1.52. Any foregoing method wherein the patient has been previously diagnosed with cancer.

The disclosure additionally provides a compound of Formula 1, e.g., PLAG, (or a pharmaceutical composition, e.g., as herein described, comprising an effective amount of a compound of Formula 1, e.g., PLAG) for use in treating, (e.g. inhibiting, reducing, controlling, mitigating, or reversing) a condition selected from leukopenia (e.g. neutropenia), and/or thrombocytopenia, e.g., for use in any of Methods 1, et. seq.

The disclosure additionally provides the use of a compound of Formula 1, e.g., PLAG, in the manufacture of a medicament for treating, (e.g. inhibiting, reducing, controlling, mitigating, or reversing) a condition selected from leukopenia (e.g. neutropenia), and/or thrombocytopenia, e.g. in any of Methods 1, et seq.

In a particular embodiment, the disclosure provides a method of treating cancer comprising administering to a patient in need thereof a chemotherapeutic agent, in conjunction with a compound of formula 1 administered in accordance with any of Methods 1, et seq., wherein the chemotherapeutic agent is administered at a dosage and/or for a period of time which would cause neutropenia and/or thrombocytopenia in the patient are the patient not receiving the compound of formula 1.

The disclosure additionally provides a method for improving the quality of life of a patient receiving chemotherapy and/or radiation therapy, comprising administering an effective amount of a compound of formula 1, especially PLAG, for example to reduce chemotherapy-induced fatigue or mucositis, e.g. by administering the compound of formula 1 in accordance with any of Methods 1, et. seq.

The disclosure provides, in another aspect, a method (Method 2) for treating, controlling or mitigating neutropenia and/or thrombocytopenia in a patient receiving a chemotherapeutic agent, for example lenalidomide, to treat a cancer which is stimulated or exacerbated by G-CSF (e.g., a bone marrow malignancy, for example multiple myeloma, acute myeloid leukemia, chronic myelogenous leukemia or myelodysplastic syndrome), the method comprising administering of an effective amount of a compound of Formula 1:

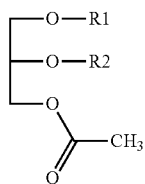

wherein $R_1$ and $R_2$ are independently a fatty acid group of 14 to 22 carbon atoms, e.g., PLAG, to a patient in need thereof; e.g., in accordance with any of Methods 1, et. seq., for example, 2.1. Method 2 wherein $R_1$ and $R_2$ are independently selected from the group consisting of palmitoyl, oleoyl, linoleoyl, linolenoyl, stearoyl, myristoyl, and arachidonoyl.

2.2. Method 2 or 2.1 wherein the Compound of Formula 1 is a compound of Formula 2:

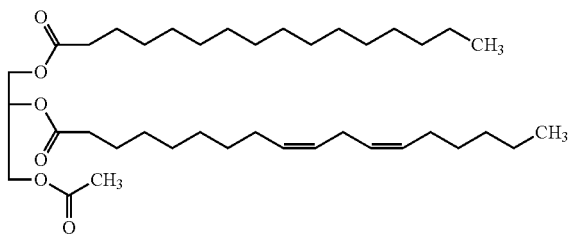 [SMILES: CCCCC/C=C\C/C=C\CCCCCCCC(=O)OC(COC(C)=O)COC(=O)CCCCCCCCCCCCCCC]

2.3. Method 2.2 wherein the Compound of Formula 2 is administered in a pharmaceutical composition that is substantially free of other monoacetyldiacylglycerols, e.g, wherein at least 95%, for example at least 99% of the total monoacetyldiacylglycerols in the formulation are of Formula 2.

2.4. Any foregoing method wherein the Compound of Formula 1 is separated or extracted from natural deer antler.

2.5. Any foregoing method wherein the Compound of Formula 1 is produced by chemical synthesis.

2.6. Any foregoing method wherein the Compound of Formula 1 is administered in the form of a pharmaceutical composition for oral administration.

2.7. Any foregoing method wherein the Compound of Formula 1 is administered in the form of a pharmaceutical composition which is a soft gelatin capsule containing the Compound of Formula 1 in combination or association with a pharmaceutically acceptable diluent or carrier, for example wherein the pharmaceutically acceptable diluent or carrier comprises an edible oil, e.g., a vegetable oil, for example olive oil.

2.8. Any foregoing method wherein the Compound of Formula 1 is administered in the form of a pharmaceutical composition comprising 0.0001 to 100.0 weight %, for example 50-95%, by weight of the composition.

2.9. Any foregoing method wherein the Compound of Formula 1 is a compound of Formula 2 administered in the form of a soft gelatin capsule containing 250 mg of the Compound of Formula 2 in combination or association with approximately 50 mg of a pharmaceutically acceptable diluent or carrier, for example an edible oil, e.g., a vegetable oil, e.g., olive oil.

2.10. Any of Method 2-2.5 wherein the Compound of Formula 1 is administered in the form of a functional food, for example as an additive or admixture to a food suitable for human consumption.

2.11. Any foregoing method wherein the Compound of Formula 1 is administered once a day (q.d.) or twice a day (b.i.d.).

2.12. Any foregoing method wherein the total daily dosage of the Compound of Formula 1 250 mg to 2000 mg/day, for example 500 mg-1500 mg/day, e.g., 500 mg/day, 1000 mg/day, or 1500 mg/day.

2.13. Any foregoing method wherein the Compound of Formula 1 is administered in a dosage of 500 mg twice a day, e.g., morning and evening.

2.14. Any foregoing method wherein the Compound of Formula 1 is administered in a dosage of 500 mg once a day, e.g., in the evening.

2.15. Any foregoing method wherein the Compound of Formula 1 is administered with food, e.g., after dinner.

2.16. Any of the foregoing methods wherein the compound of formula 1 is administered over a period of at least two weeks, e.g., at least a month.

2.17. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

2.18. Any foregoing method wherein the chemotherapeutic agent is selected from one or more of cyclophosphamide, doxorubicin, etoposide, ifosfamide, mesna, cisplatin, gemcitabine, tamoxifen and lenalidomide.

2.19. Any foregoing method wherein the chemotherapeutic agent is lenalidomide.

2.20. Any foregoing method wherein the cancer is multiple myeloma.

2.21. Any foregoing method wherein the cancer is chronic myelogenous leukemia (CML).

2.22. Any foregoing method wherein the cancer is acute myeloid leukemia.
2.23. Any foregoing method wherein the cancer is myelodysplastic syndrome.
2.24. Any of the foregoing methods wherein the patient is
  01.24.1. Intending to receive chemotherapy at a dose sufficient to cause neutropenia in the absence of other treatment, or
  01.24.2. suffering from neutropenia consequent to chemotherapy.
2.25. Any of the foregoing methods wherein the patient is a cancer patient, the compound of formula 1 is administered prior to myeloablative chemotherapy, to enhance levels of peripheral blood progenitor cells, which are collected for reintroduction to the patient subsequent to myeloablative chemotherapy, and optionally, the compound of formula is also administered subsequently to myeloablative chemotherapy.
2.26. Any of the foregoing methods wherein "neutropenia" is considered to be a count of 2000 or fewer, e.g., 1,700 or fewer, e.g. 1500 Or fewer neutrophils per microliter of blood.
2.27. Any of the foregoing methods wherein treatment is continued until the patient has at least 5000, e.g., at least 8000, e.g. at least 10,000 neutrophils per microliter of blood.
2.28. Any of the foregoing methods wherein the neutropenia is associated with fever.
2.29. Any of the foregoing methods wherein the patient suffers from or is at risk of neutropenia or thrombocytopenia due to treatment with one or more chemotherapeutic agents selected from cyclophosphamide, doxorubicin, etoposide, ifosfamide, mesna, cisplatin, gemcitabine, and tamoxifen.
2.30. Any foregoing method wherein the condition to be treated includes thrombocytopenia, e.g. wherein thrombocytopenia is considered to be less than 130,000, e.g., less than 100,000, e.g., less than 50,000 platelets per microliter (µl) of blood.
2.31. Any foregoing method wherein the patient suffers from chronic thrombocytopenia, e.g., due to cancer, viral infection, aplastic anemia, immune thrombocytic purpura (ITP), thrombotic thrombocytopenic purpura (TTP) or liver disease.
2.32. Any of the foregoing methods wherein treatment is continued until the patient has at least 50,000, e.g., at least 100,000, e.g. at least 130,000 platelets per microliter of blood.
2.33. Any foregoing method wherein the compound of formula 1 is administered in accordance with any of Methods 1, et seq.

The disclosure additionally provides a compound of Formula 1, e.g., PLAG, (or a pharmaceutical composition, e.g., as herein described, comprising an effective amount of a compound of Formula 1, e.g., PLAG) for use in combination with a chemotherapeutic agent, e.g., lenalidomide e.g., for use in any of Methods 2, et. seq.

The disclosure additionally provides the use of a compound of Formula 1, e.g., PLAG, in the manufacture of a medicament for use in combination with a chemotherapeutic agent, e.g., lenalidomide e.g., for use in any of Methods 2, et. seq.

In another aspect, the disclosure provides a method (Method 3) for treating a blood cancer, e.g., a bone marrow malignancy, for example a blood cancer which may be induced or exacerbated by G-CSF, e.g., selected from multiple myeloma, acute myeloid leukemia, chronic myelogenous leukemia and myelodysplastic syndrome, comprising co-administering (sequentially or simultaneously) an effective amount of (i) a chemotherapeutic agent, e.g., lenalidomide, and (ii) a compound of Formula 1:

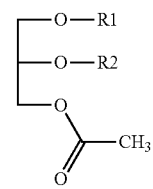

wherein R1 and R2 are independently a fatty acid group of 14 to 22 carbon atoms, e.g., PLAG, to a patient in need thereof;
for example,
  3.1. Method 3 wherein R1 and R2 are independently selected from the group consisting of palmitoyl, oleoyl, linoleoyl, linolenoyl, stearoyl, myristoyl, and arachidonoyl.
  3.2. Method 3 or 3.1 wherein the Compound of Formula 1 is a compound of Formula 2:

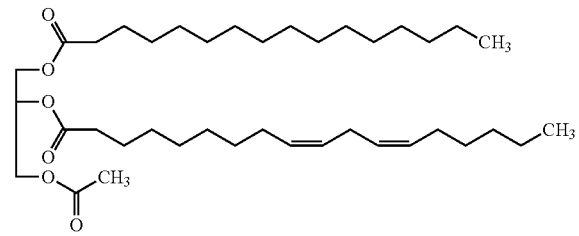 [SMILES: CCCCC/C=C\C/C=C\CCCCCCCC(=O)OC(COC(C)=O)COC(=O)CCCCCCCCCCCCCCC]

3.3. Method 3.2 wherein the Compound of Formula 2 is administered in a pharmaceutical composition which is substantially free of other monoacetyldiacylglycerols, e.g, wherein at least 95%, for example at least 99% of the total monoacetyldiacylglycerols in the formulation are of Formula 2.
  3.4. Any foregoing method wherein the Compound of Formula 1 is separated or extracted from natural deer antler.
  3.5. Any foregoing method wherein the Compound of Formula 1 is produced by chemical synthesis.
  3.6. Any foregoing method wherein the Compound of Formula 1 is administered in the form of a pharmaceutical composition for oral administration.
  3.7. Any foregoing method wherein the Compound of Formula 1 is administered in the form of a pharmaceutical composition which is a soft gelatin capsule containing the Compound of Formula 1 in combination or association with a pharmaceutically acceptable diluent or carrier, for example wherein the pharmaceutically acceptable diluent or carrier comprises an edible oil, e.g., a vegetable oil, for example olive oil.
  3.8. Any foregoing method wherein the Compound of Formula 1 is administered in the form of a pharmaceutical composition comprising 0.0001 to 100.0 weight %, for example 50-95%, by weight of the composition.
  3.9. Any foregoing method wherein the Compound of Formula 1 is a compound of Formula 2 administered in the form of a soft gelatin capsule containing 250 mg of the Compound of Formula 2 in combination or association with approximately 50 mg of a pharmaceutically acceptable diluent or carrier, for example an edible oil, e.g., a vegetable oil, e.g., olive oil.
3.10. Any of Method 3-3.5 wherein the Compound of Formula 1 is administered in the form of a functional food, for example as an additive or admixture to a food suitable for human consumption.
3.11. Any foregoing method wherein the Compound of Formula 1 is administered once a day (q.d.) or twice a day (b.i.d.).
3.12. Any foregoing method wherein the total daily dosage of the Compound of Formula 1 250 mg to 2000 mg/day, for example 500 mg-1500 mg/day, e.g., 500 mg/day, 1000 mg/day, or 1500 mg/day.
3.13. Any foregoing method wherein the Compound of Formula 1 is administered in a dosage of 500 mg twice a day, e.g., morning and evening.
3.14. Any foregoing method wherein the Compound of Formula 1 is administered in a dosage of 500 mg once a day, e.g., in the evening.
3.15. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.
3.16. Any foregoing method wherein the Compound of Formula 1 is administered with food, e.g., after dinner.
3.17. Any of the foregoing methods wherein the compound of formula 1 is administered over a period of at least two weeks, e.g., at least a month.
3.18. Any foregoing method wherein the chemotherapeutic agent is selected from one or more of cyclophosphamide, doxorubicin, etoposide, ifosfamide, mesna, cisplatin, gemcitabine, tamoxifen and lenalidomide.
3.19. Any foregoing method wherein the chemotherapeutic agent is lenalidomide.
3.20. Any foregoing method wherein the cancer is multiple myeloma.
3.21. Any foregoing method wherein the cancer is chronic myelogenous leukemia (CML).
3.22. Any foregoing method wherein the cancer is acute myeloid leukemia.
3.23. Any foregoing method wherein the cancer is myelodysplastic syndrome.
3.24. Any of the foregoing methods wherein the patient is
  0.24.1. Intending to receive chemotherapy at a dose sufficient to cause neutropenia in the absence of other treatment, or
  0.24.2. suffering from neutropenia consequent to chemotherapy.
3.25. Any of the foregoing methods wherein the patient is a cancer patient, the compound of formula 1 is administered prior to myeloablative chemotherapy, to enhance levels of peripheral blood progenitor cells, which are collected for reintroduction to the patient subsequent to myeloablative chemotherapy, and optionally, the compound of formula is also administered subsequently to myeloablative chemotherapy.
3.26. Any of the foregoing methods wherein treatment is continued until the patient has at least 5000, e.g., at least 8000, e.g. at least 10,000 neutrophils per microliter of blood.
3.27. Any foregoing method wherein the compound of formula 1 is administered in accordance with any of Methods 1, et seq.

The disclosure additionally provides a compound of Formula 1, e.g., PLAG, (or a pharmaceutical composition, e.g., as herein described, comprising an effective amount of a compound of Formula 1, e.g., PLAG) for use in treating a blood cancer, e.g., a bone marrow malignancy, for example a blood cancer which may be induced or exacerbated by G-CSF, e.g., selected from multiple myeloma, acute myeloid leukemia, chronic myelogenous leukemia and myelodysplastic syndrome, in conjunction with co-administration (sequentially or simultaneously) of an effective amount of a chemotherapeutic agent, e.g., lenalidomide, e.g., for use in any of Methods 3, et. seq.

The disclosure additionally provides the use of a compound of Formula 1, e.g., PLAG, in the manufacture of a medicament for treating a blood cancer, e.g., a bone marrow malignancy, for example a blood cancer which may be induced or exacerbated by G-CSF, e.g., selected from multiple myeloma, acute myeloid leukemia, chronic myelogenous leukemia and myelodysplastic syndrome, in conjunction with co-administration (sequentially or simultaneously) of an effective amount of a chemotherapeutic agent, e.g., lenalidomide, e.g., for use in any of Methods 3, et. seq.

In another aspect, the disclosure provides a method (Method 4) for treatment (including prophylaxis) of neutropenia and/or for mobilizing peripheral blood progenitor cells (PBPCs), comprising administering (sequentially or simultaneously) an effective amount of (i) a compound of Formula 1:

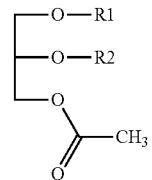

wherein $R_1$ and $R_2$ are independently a fatty acid group of 14 to 22 carbon atoms, e.g., PLAG, and (ii) a G-CSF, e.g., selected from filgrastim, pegfilgrastim, and lenograstim, to a patient in need thereof; for example,
  4.1. Method 4 wherein $R_1$ and $R_2$ are independently selected from the group consisting of palmitoyl, oleoyl, linoleoyl, linolenoyl, stearoyl, myristoyl, and arachidonoyl.
  4.2. Method 4 or 4.1 wherein the Compound of Formula 1 is a compound of Formula 2:

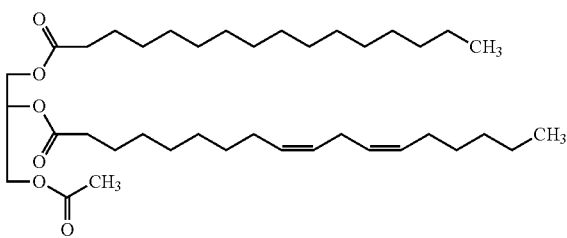

4.3. Method 4.2 wherein the Compound of Formula 2 is administered in a pharmaceutical composition which is substantially free of other monoacetyldiacylglycerols, e.g, wherein at least 95%, for example at least 99% of the total monoacetyldiacylglycerols in the formulation are of Formula 2.

4.4. Any foregoing method wherein the Compound of Formula 1 is separated or extracted from natural deer antler.

4.5. Any foregoing method wherein the Compound of Formula 1 is produced by chemical synthesis.

4.6. Any foregoing method wherein the Compound of Formula 1 is administered in the form of a pharmaceutical composition for oral administration.

4.7. Any foregoing method wherein the Compound of Formula 1 is administered in the form of a pharmaceutical composition which is a soft gelatin capsule containing the Compound of Formula 1 in combination or association with a pharmaceutically acceptable diluent or carrier, for example wherein the pharmaceutically acceptable diluent or carrier comprises an edible oil, e.g., a vegetable oil, for example olive oil.

4.8. Any foregoing method wherein the Compound of Formula 1 is administered in the form of a pharmaceutical composition comprising 0.0001 to 100.0 weight %, for example 50-95%, by weight of the composition.

4.9. Any foregoing method wherein the Compound of Formula 1 is a compound of Formula 2 administered in the form of a soft gelatin capsule containing 250 mg of the Compound of Formula 2 in combination or association with approximately 50 mg of a pharmaceutically acceptable diluent or carrier, for example an edible oil, e.g., a vegetable oil, e.g., olive oil.

4.10. Any of Method 4-4.5 wherein the Compound of Formula 1 is administered in the form of a functional food, for example as an additive or admixture to a food suitable for human consumption.

4.11. Any foregoing method wherein the Compound of Formula 1 is administered once a day (q.d.) or twice a day (b.i.d.).

4.12. Any foregoing method wherein the total daily dosage of the Compound of Formula 1 250 mg to 2000 mg/day, for example 500 mg-1500 mg/day, e.g., 500 mg/day, 1000 mg/day, or 1500 mg/day.

4.13. Any foregoing method wherein the Compound of Formula 1 is administered in a dosage of 500 mg twice a day, e.g., morning and evening.

4.14. Any foregoing method wherein the Compound of Formula 1 is administered in a dosage of 500 mg once a day, e.g., in the evening.

4.15. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

4.16. Any foregoing method wherein the Compound of Formula 1 is administered with food, e.g., after dinner.

4.17. Any of the foregoing methods wherein the compound of formula 1 is administered over a period of at least two weeks, e.g., at least a month.

4.18. Any of the foregoing methods wherein the G-CSF is selected from filgrastim, pegfilgrastim, and lenograstim, e.g., wherein the G-CSF is filgrastim.

4.19. Any of the foregoing methods wherein the patient is
   01.19.1. Intending to receive chemotherapy at a dose sufficient to cause neutropenia in the absence of other treatment, or
   01.19.2. suffering from neutropenia consequent to chemotherapy.

4.20. Any of the foregoing methods wherein the patient is a cancer patient receiving myelosuppressive chemotherapy.

4.21. Any of the foregoing methods wherein the patient is a cancer patient receiving myelosuppressive chemotherapy, wherein the treatment with the compound of Formula 1 and the G-CSF is suspended for a period at least 24 hours prior until at least 24 hours after the administration of the chemotherapy, e.g., to reduce the vulnerability of cells stimulated by the compound of Formula 1 and the G-CSF to the chemotherapy.

4.22. Any of the foregoing methods wherein the patient is a cancer patient receiving a bone marrow transplant.

4.23. Any of the foregoing methods wherein the patient is a cancer patient, the compound of formula 1 and G-CSF are administered prior to myeloablative chemotherapy, to enhance levels of peripheral blood progenitor cells, which are collected for reintroduction to the patient subsequent to myeloablative chemotherapy, and optionally, the compound of formula 1 and G-CSF are also administered subsequently to myeloablative chemotherapy.

4.24. Any foregoing method wherein the patient suffers from chronic neutropenia, e.g., congenital neutropenia, cyclic neutropenia or idiopathic neutropenia.

4.25. Any of the foregoing methods wherein "neutropenia" is considered to be a count of 2000 or fewer, e.g., 1,700 or fewer, e.g. 1500 Or fewer neutrophils per microliter of blood.

4.26. Any of the foregoing methods wherein treatment is continued until the patient has at least 5000, e.g., at least 8000, e.g. at least 10,000 neutrophils per microliter of blood.

4.27. Any of the foregoing methods wherein the neutropenia is associated with fever.

4.28. Any of the foregoing methods wherein the Compound of Formula 1 is administered in an amount effective to mitigate or treat side effects of G-CSF, e.g., thrombocytopenia and/or bone pain induced by G-CSF.

4.29. Any of the foregoing methods wherein the patient suffers from or is at risk of neutropenia due to treatment with one or more chemotherapeutic agents selected from cyclophosphamide, doxorubicin, etoposide, ifosfamide, mesna, cisplatin, gemcitabine, and tamoxifen.

4.30. Any foregoing method wherein the compound of formula 1 is administered in accordance with any of Methods 1, et seq.

The disclosure additionally provides a method (Method 5) to mitigate or treat side effects of G-CSF, e.g., thrombocytopenia and/or bone pain induced by G-CSF, comprising co-administering, sequentially or simultaneously, a compound of formula 1, e.g., PLAG, to a patient in need thereof, e.g., in a regimen as described in any of Methods 1, et seq.

The disclosure additionally provides a compound of Formula 1, e.g., PLAG, (or a pharmaceutical composition, e.g., as herein described, comprising an effective amount of a compound of Formula 1, e.g., PLAG) for use in combination with a G-CSF, e.g., for use in any of Methods 1, et. seq., Method 4, et seq., or Method 5.

The disclosure additionally provides the use of a compound of Formula 1, e.g., PLAG, in the manufacture of a medicament for use in combination with a G-CSF, e.g., for use in any of Methods 1, et. seq. or Methods 4, et seq., or Method 5.

The disclosure additionally provides a method (Method 6) of treating anemia comprising administering an effective amount of a compound of Formula 1:

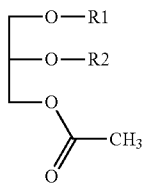

wherein $R_1$ and $R_2$ are independently a fatty acid group of 14 to 22 carbon atoms, e.g., PLAG, to a patient in need thereof; for example, 6.1. Method 6 wherein $R_1$ and $R_2$ are independently selected from the group consisting of palmitoyl, oleoyl, linoleoyl, linolenoyl, stearoyl, myristoyl, and arachidonoyl.

6.2. Method 6 or 6.1 wherein the Compound of Formula 1 is a compound of Formula 2:

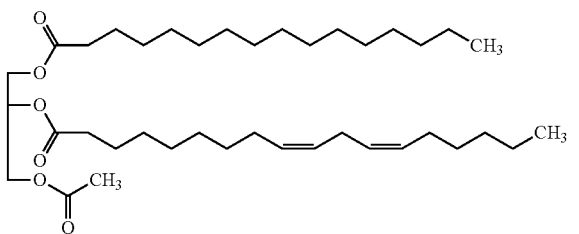 [SMILES: CCCCC/C=C\C/C=C\CCCCCCCC(=O)OC(COC(C)=O)COC(=O)CCCCCCCCCCCCCCC]

6.3. Method 6.2 wherein the Compound of Formula 2 is administered in a pharmaceutical composition which is substantially free of other monoacetyldiacylglycerols, e.g, wherein at least 95%, for example at least 99% of the total monoacetyldiacylglycerols in the formulation are of Formula 2.

6.4. Any foregoing method wherein the Compound of Formula 1 is separated or extracted from natural deer antler.

6.5. Any foregoing method wherein the Compound of Formula 1 is produced by chemical synthesis.

6.6. Any foregoing method wherein the Compound of Formula 1 is administered in the form of a pharmaceutical composition for oral administration.

6.7. Any foregoing method wherein the Compound of Formula 1 is administered in the form of a pharmaceutical composition which is a soft gelatin capsule containing the Compound of Formula 1 in combination or association with a pharmaceutically acceptable diluent or carrier, for example wherein the pharmaceutically acceptable diluent or carrier comprises an edible oil, e.g., a vegetable oil, for example olive oil.

6.8. Any foregoing method wherein the Compound of Formula 1 is administered in the form of a pharmaceutical composition comprising 0.0001 to 100.0 weight %, for example 50-95%, by weight of the composition.

6.9. Any foregoing method wherein the Compound of Formula 1 is a compound of Formula 2 administered in the form of a soft gelatin capsule containing 250 mg of the Compound of Formula 2 in combination or association with approximately 50 mg of a pharmaceutically acceptable diluent or carrier, for example an edible oil, e.g., a vegetable oil, e.g., olive oil.

6.10. Any of Method 6-6.5 wherein the Compound of Formula 1 is administered in the form of a functional food, for example as an additive or admixture to a food suitable for human consumption.

6.11. Any foregoing method wherein the Compound of Formula 1 is administered once a day (q.d.) or twice a day (b.i.d.).

6.12. Any foregoing method wherein the total daily dosage of the Compound of Formula 1 250 mg to 2000 mg/day, for example 500 mg-1500 mg/day, e.g., 500 mg/day, 1000 mg/day, or 1500 mg/day.

6.13. Any foregoing method wherein the Compound of Formula 1 is administered in a dosage of 500 mg twice a day, e.g., morning and evening.

6.14. Any foregoing method wherein the Compound of Formula 1 is administered in a dosage of 500 mg once a day, e.g., in the evening.

6.15. Any foregoing method wherein the compound of formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

6.16. Any foregoing method wherein the Compound of Formula 1 is administered with food, e.g., after dinner.

6.17. Any of the foregoing methods wherein the compound of formula 1 is administered over a period of at least two weeks, e.g., at least a month.

6.18. Any of the foregoing methods wherein the patient also suffers from thrombocytopenia.

6.19. Any foregoing method wherein the patient is receiving chemotherapy and/or radiation therapy.

6.20. Any foregoing method wherein the anemia is normocytic anemia.

6.21. Any foregoing method wherein the anemia is caused by active bleeding, for example from heavy menstrual bleeding, wounds, gastrointestinal ulcers, or cancer, e.g. for example cancer of the colon.

6.22. Any foregoing method wherein the anemia is of myelodysplastic origin.

6.23. Any foregoing method wherein the patient has a hemoglobin level of less than 12 g/dL.

6.24. Any foregoing method wherein the treatment is continued until the patient has a hemoglobin level of at least 12 g/dL.

6.25. Any foregoing method where the patient also receives supplemental iron. 6.26. Any foregoing method wherein the compound of formula 1 is administered in accordance with any of Methods 1, et seq.

The disclosure additionally provides a compound of Formula 1, e.g., PLAG, (or a pharmaceutical composition, e.g., as herein described, comprising an effective amount of a compound of Formula 1, e.g., PLAG) for use in treating anemia, e.g., for use in any of Methods 6, et. seq., The disclosure additionally provides the use of a compound of Formula 1, e.g., PLAG, in the manufacture of a medicament for treating anemia, e.g., for use in any of Methods 6, et. seq., As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless otherwise specified, all percentages and amounts expressed herein and elsewhere in the specification should be understood to refer to percentages by weight. The amounts given are based on the active weight of the material.

The following examples are provided for better understanding of this invention. However, the present disclosure is not limited by the examples.

Example 1—In Vitro Inhibition of PKCθ/p38/ERK Activity in RBL-2H3 Cells

In vitro pharmacology studies in cell lines show that PLAG is capable of inhibiting the PKCθ/p38 MAPK/ERK pathway, which is involved in the maturation of lymphoid progenitor cells from HSC. Dephosphorylation of p38 MAPK and ERK1/2 in PLAG-treated RBL-2H3 cells is determined by western blot analysis using anti-phospho-p38 and anti-phospho-ERK1/2 respectively. To activate the p38 and ERK1/2 in RBL-2H3 cells, the cells are sensitized with 50 ng/mL of anti-DNP-IgE overnight. After washing with PBS three times, 20 ng/ml of DNP-HSA is added. Each cell lysate for western blot is prepared in the PLAG-treated RBL-2H3 cells in a dose-dependent manner and incubated for the same time (15 min). β-actin is used as internal controls. ERK1/2 and p38 phosphorylation start immediately after IgE-antigen complex stimulation and remain sufficiently activated for 5 min. However, when IgE-antigen complex stimulation is exerted in PLAG pre-incubated RBL-2H3 cells, ERK1/2 and p38 phosphorylation is down-regulated. The western blot shows the inhibitory effect of PLAG on the activation of p38 MAP kinases and ERK1/2 (MEK1/2) in IgE-antigen complex stimulated RBL-2H3 cells.

Example 2—In Vitro Inhibition of Complement Activation Pathway

PLAG's activity for regulating complement activity is achieved by suppressing production of C3. The production of C3 depends on the activity of STAT6. Thus, it is hypothesized that PLAG suppresses the activity of STAT6, and thereby suppresses the production of C3, which is up-regulated or activated by chemotherapy.

Dephosphorylation of STAT6 in PLAG Treated Cells:

Dephosphorylation of STAT6 is examined using anti-phosphorylated STAT6 in U937, A549, and Jurkat cell lysates treated with PLAG concentration from 0.01 to 10 μg/ml. Phosphorylation of STAT6 is induced by treatment with 10 ng/ml of IL-4. Dephosphorylation of STAT1 is examined in the U937 cell lysate treated with PLAG (0.01 to 10 μg/ml). Phosphorylation of STAT1 is induced by 10 ng of IFN-γ treatment. Dephosphorylation of STAT1 and STAT6 is examined at 15 min after stimulation with IFN-γ and IL-4 respectively, in the PLAG pretreated cells. Western blot analysis shows activities of STAT6 and STAT1. The transcriptional activity of STAT6 is decreased by the dephosphorylation of STAT6. In lymphoma-derived cell line U937, T cell-derived Jurkat cells, and lung epithelial cell line A549, IL-4 treatment induced STAT6 phosphorylation is inhibited with increasing PLAG concentrations. No effect of PLAG on STAT1 phosphorylation is observed.

Activity of STAT6:

By using STAT6 inhibitor (S6I), it is confirmed that the reduction of Complement 3 in HepG2 cells (human hepatocyte cell line) is regulated by STAT6. When treating HepG2 cells with PLAG, the transcriptional activity of STAT6 is gradually decreased in accordance with the amount of PLAG as confirmed by a luciferase activity study. It is also confirmed that PLAG has selective efficacy on STAT6 over STAT1. FIG. 1 presents graphs showing STAT1 and STAT6 transcriptional activity in the PLAG treated HepG2 cells. NC refers to the unstimulated control cell. For the STAT1 assay, gene transfected HepG2 (human hepatocyte cell line) is treated with 10 ng of IFN-γ and serially diluted PLAG is added (0.01 μg/ml, 0.1 μg/ml, 1 μg/ml, and 10 μg/ml as shown) to see its effect on gene expression in the stimulated cell. For the STAT6 assay, gene transfected HepG2 cells are treated with 10 ng of IL-4 and again serially diluted PLAG is added (0.01 μg/ml, 0.1 μg/ml, 1 μg/ml, and 10 μg/ml as shown) to see its effect on gene expression in the stimulated cell. The assay is carried out following 12 hours incubation of treated cells. PLAG has no effect on STAT1 expression in this assay, but has a significant, dose-dependent effect on STAT6 expression.

In Vitro Inhibition of C3 Expression in Human HMC-1 Cells:

Published reports on the role of a complement-dependent mechanism in drug induced neutropenia and the role of neutrophils in vascular inflammation and the response to sepsis suggest that complement activation may be involved in the thrombocytopenia and leukopenia induced by chemotherapy. We have found that PLAG can down-regulate C3 to attenuate complement activation; PLAG treated human monocyte cells (HMC-1) and PLAG treated hepatocytes (HepG2) show reduced expression of C3.

A blood cell line, HMC-1 (human mast cell, American Type Culture Collection, ATCC, Rockville, Md.) is incubated and maintained at 37° C. under 5% $CO_2$ humid conditions. The medium is IMDM (Life Technologies, Karlsruhe, Germany) containing 10% Fetal Calf Serum (FCS, HyClone, Logan, Utah), 2 mM L-glutamate, 100 μg/ml penicillin, 100 μg/ml streptomycin (Life Technologies). The cultured HMC-1 cells (1×106 cell/ml) are pretreated with 0.1 and 1 μg/mL concentration of PLAG, followed by treating with IL-4 (5 ng) and/or TNF-α (10 ng) to induce cellular activities.

The expressed C3 and its mRNA level change are observed by using RT-PCR (Reverse Transcriptase Polymerase Chain Reaction). The RT-PCR is carried out as follows: the total RNA is separated by the standard protocol and cDNA is synthesized using AccuScript High Fidelity 1st Strand cDNA Synthesis Kit (Stratagene) by the manufacturer's instructions. Two-step RT-PCR reaction is conducted using Oligo-dT primer and reverse transcriptase, pair of primer and Taq polymerase (Takara, Shiga, Japan). The synthesized cDNA (1 μl) is used for 20 μl PCR reaction with 0.5 U ExTaq DNA polymerase, 1 buffer and 1 mM dNTP mix (Takara) and the primer pair. PCR amplification is conducted under the following conditions using GeneAmp PCR system 2700 (Applied Biosystems, Foster city, Calif., USA); 5 minutes at 94° C., followed by 45 seconds at 94° C., 45 seconds at 56° C. and 1 minute at 72° C. with 25-40 cycles and the final extension reaction is performed for 7 minutes at 72° C. The PCR primer used for cDNA amplification is designed with Primer3 program, and purchased from Bioneer (Daejeon, KOREA). The product of PCR is separated using 1.5% agarose gel, dyed with ethidium bromide (EtBr), and visualized with Gel Doc 2000 UV trans-illuminator (Bio-Rad Laboratories, Hercules, Calif., USA), and the experimental data is analyzed using Quantity One software (Bio-Rad Laboratories). Western blots show that treatment of HMC-1 cell with IL-4 and TNF-α results in expression of C3, which is suppressed by PLAG on a concentration dependent basis, comparable to cells treated with IL-4 and TNF-α, followed by treatment with S6I (signal transducer and activator of transcription 6 (STAT6) inhibitor, AS1517499, Axon Medchem, Netherlands). STAT6 inhibitor blocks the STAT6 signal transduction in the cell by IL-4, which in turn suppresses expression of C3. These data suggest that PLAG may work in a manner similar to the STAT6 inhibitor.

Figure 2:
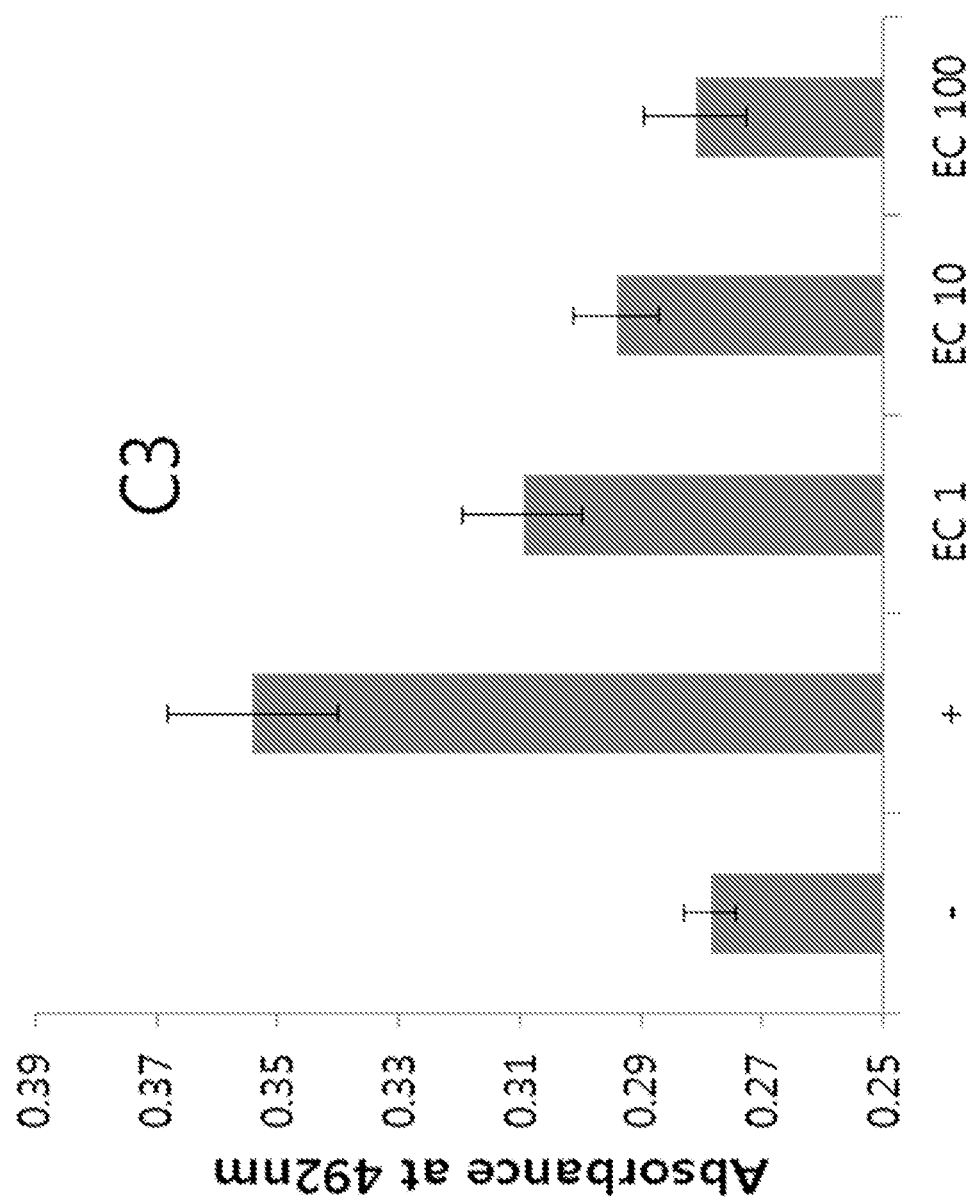
FIG. 2 depicts complement 3 inhibition by PLAG in HMC-1 cells

C3 Inhibition by PLAG in HMC-1:

In a separate experiment, human mast cells (HMC-1, 1×105 cell/ml) are treated with PLAG of various concentrations (1, 10 and 100 μg/mL) for 2 hours. The cells are activated for 72 hours with 10% FBS (Fetal bovine serum) containing IMDM. The decrease of C3 is confirmed by ELISA analysis of the expressed protein. As shown in FIG. 2, the decrease of C3 is proportional to the concentration of PLAG (PLAG is referred to as EC in that figure; units are μg/ml).

C3 Excretion from HepG2 Cell Line:

A liver cell line, HepG2 (American Type Culture Collection, ATCC, Rockville, Md.), is incubated and maintained at 37° C., 5% $CO_2$ humid atmosphere in DMEM medium. When HepG2 cells, which are known to produce complement in culture, are treated with PLAG, the activity of complement is reduced effectively, as confirmed by RT-PCR of mRNA. In the RT-PCR, 5×105 number of HepG2 cells/ml are distributed into 12 well plates and induced C3 for 12 hours with 10% FCS. Then PLAG is added and further cultured for 2 hours. Cells are harvested and mRNA is isolated and RT-PCR is carried out with specific primer of C3; GAPDH is used as an internal control. The RT-PCR shows that PLAG inhibits C3 expression somewhat at 1 microgram/ml and entirely at 10 microgram/ml, comparable to results obtained with 10 and 100 microgram/ml of S6I.

Figure 3C:
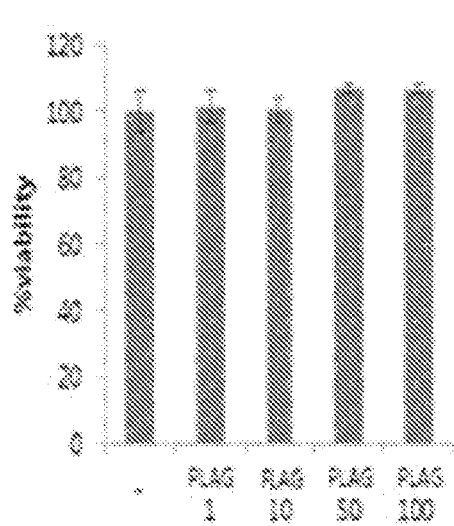
FIG. 3C shows that a similar result is obtained by the administration of S6I.
Figure 3C:
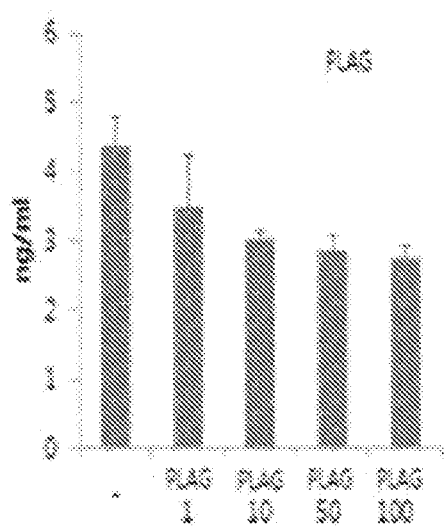
Figure 3C:
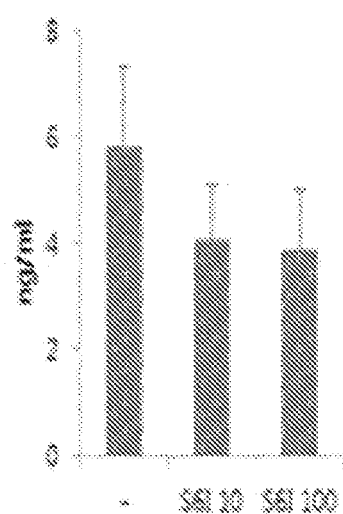

The incubated HepG2 cell lines are treated with PLAG (1~100 μg/ml), followed by IL-4 and TNF-α, reacted for 1 hour, incubated for 18 hours at 37° C. and the supernatant isolated. Quantitation of the amount of C3 in the cellular culture medium (supernatant) from HepG2 cells is performed by ELISA using a commercially available monoclonal antibody (mAb, R&D Systems) and the manufacture's protocol; the results are presented in FIG. 3. C3 is expressed spontaneously under in vitro culture condition using 10% FCS added to HepG2 cells incubated for 12 hr. The cells are treated with different doses of PLAG from 1 to 100 μg/ml (Panel A, Panel B) or 10 and 100 μg/ml of S6I (Panel C), reacted with IL-4 and TNF-α for 1 hr and then incubated for 18 hr at 37° C. Cellular viability is confirmed using the WST-1 assay (Panel A). This assay shows cell viability measured by the formation of fluorescent material, formazan, from tetrazolium salts, (WST-1) by the deoxygenase in mitochondria in the cell. FIG. 3A confirms that PLAG does not affect the cellular propagation and death. FIG. 3B shows that expression of C3 is decreased dose-dependently by the administration of PLAG and FIG. 3C shows that a similar result is obtained by the administration of S6I.

Example 3—In Vivo Effect of PLAG on Neutropenia, Thrombocytopenia and Complement Activation In Vivo in Mice Colony Forming Units in Spleen (CFUs) Assay in Vivo:

In order to determine the in vivo effect of PLAG on the recovery of hematopoiesis, a CFUs assay is performed in heavily irradiated mice. A microscopic examination of the spleens of mice treated with PLAG at a dose of 50 mg/kg/d i.p. or p.o. reveals a marked increase in the number of splenic nodules and the numbers of primitive progenitor cells and megakaryocytes in all treated animals.

Figure 4:
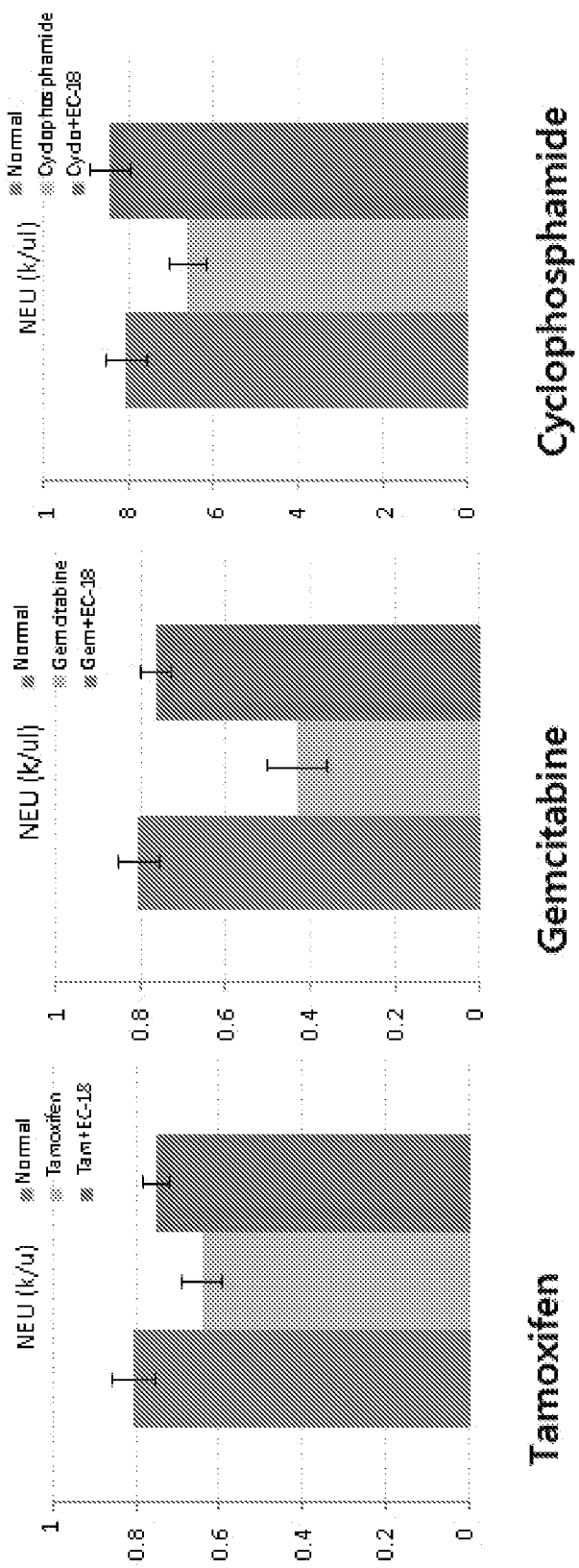
FIG. 4 depicts the neutrophil-protective effects of PLAG against three chemotherapeutic agents in a mouse model.

In Vivo Efficacy Study in Mice:

The effect of PLAG for treatment of neutropenia and thrombocytopenia induced by chemotherapy (CIN) is evaluated in an animal model. Anti-cancer agents (Gemcitabine 50 mg/kg, Cyclosphosphamide 100 mg/, or Tamoxifen 50 mg/kg) are dosed daily for 3 weeks; PLAG is also administered 50 mg/kg daily for 3 weeks. After three weeks, neutrophils are harvested and counted with Auto Hematology Analyzer BC-5300. As shown in FIG. 4, the reduced neutrophil count following chemotherapy is prevented by the treatment with PLAG. Mice treated only with Tamoxifen show extreme weight loss, dehydration, and loss of activity to retreat, compared to the group co-treated with PLAG, which show faster improvement of activities and survival rate. In the mice group treated with PLAG and Gemcitabine, the neutrophil score improved significantly. Even though gemcitabine reduces the neutrophil count in animals receiving co-administration of PLAG initially, the neutrophil count recovers to normal and is maintained at normal levels, and continued administration of PLAG results in an improved survival rate compared to Gemcitabine alone treated group. In the mice group treated with PLAG and cyclophosphamide the neutrophil count is also improved significantly compared to the control group.

Figure 5:
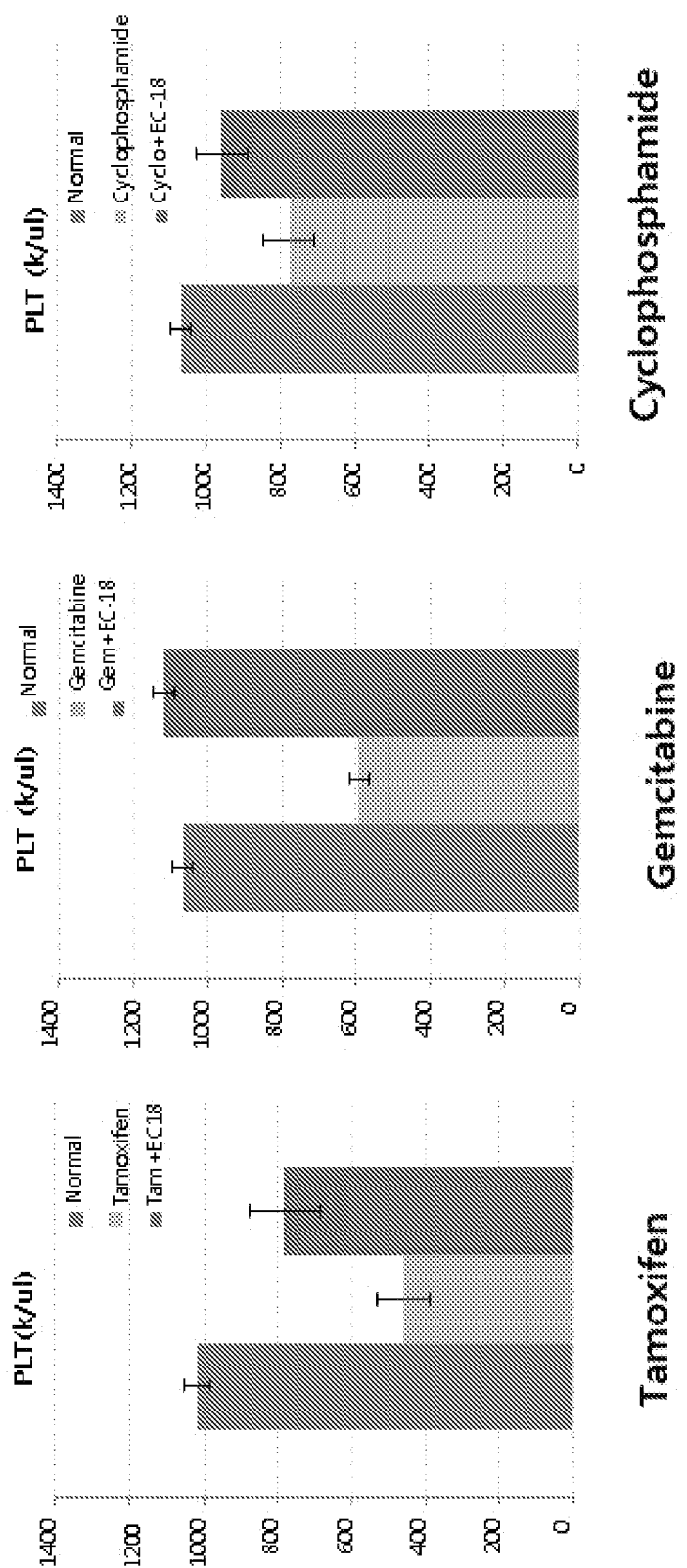
FIG. 5 depicts the platelet-protective effects of PLAG against three chemotherapeutic agents in a mouse model.

Data on platelet counts is depicted in FIG. 5, showing that PLAG provides a similar protective effect for platelets against Gemcitabine 50 mg/kg, Cyclosphosphamide 100 mg/, or Tamoxifen 50 mg/kg.

Figure 6:
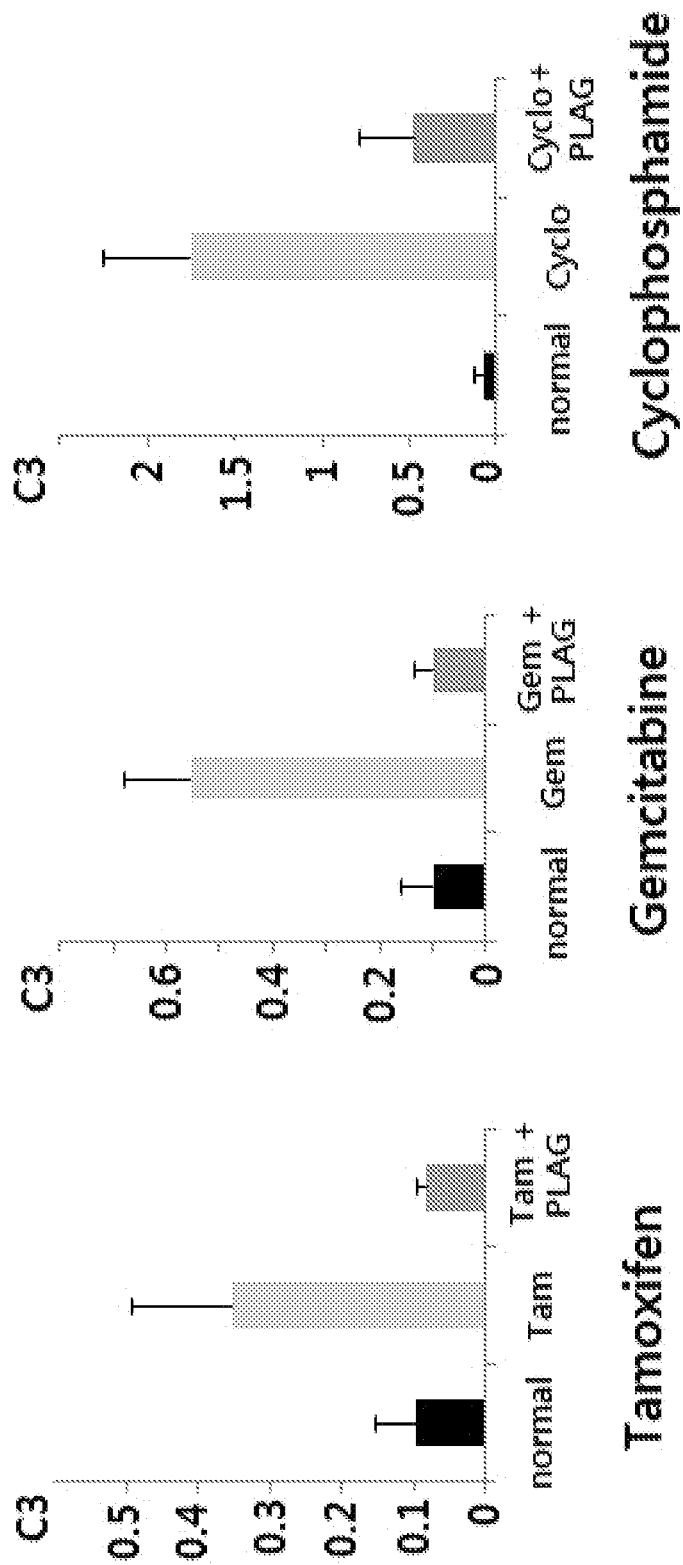
FIG. 6 depicts the complement 3 activation effects of three chemotherapeutic agents in a mouse model, and the blockage of these effects by PLAG.

It is believed that the neutropenia and thrombocytopenia of these agents and other chemotherapeutic agents may be due at least in part to a specific complement-mediated toxicity. This is seen in FIG. 6. All of these agents significantly activate Complement 3, and this activity is largely blocked by PLAG.

Example 4—In Vivo Protection Against Thrombocytopenia in Mice

To evaluate the effect of PLAG on the concentration of platelets mice are treated with compounds which would be expected to cause reductions in platelet numbers, specifically phenylhydrazine, tamoxifen or lipopolysaccharide.

Mice are injected with 100 mg/kg phenylhydrazine (PHZ), i.p., to induce anemia and reduction of platelets. 5 mg/kg PLAG is administered to the mice orally and blood samples are taken at 3 and 13 days after. In addition, for comparison, normal mice which are not treated with phenylhydrazine are prepared as a normal group, and mice treated with PHZ and olive oil instead of PLAG are prepared as a control group. The blood samples taken from the mice are treated with 0.5 ml EDTA (Minicollect tube, Greiner bio-one, Austria) and concentration of platelet is measured using automated blood sample analyzer BC-6800 (Mindray, Shenzhen, China) by number of platelet per mL (k: 1,000). The results are shown in Table 1.

TABLE 1

| | normal | PHZ + oil treated control group (day 3) | PHZ + PLAG treated group (day 3) |
| --- | --- | --- | --- |
| Platelet (day 3) Conc (k/ul) | 964.4 ± 57.4 | 851 ± 44.5 | 1072 ± 125.4 |
| Platelet (day 13) Conc (k/ul) | 1002.4 ± 36.8 | 1051 ± 55.4 | 1188.8 ± 115.6 |

The experiment is repeated using Tamoxifen (Tam), an anticancer agent, injected at the amount of 100 mg/kg, or lipopolysaccharide (LPS), an inflammation inducer, at the amount of 1 mg/kg to induce platelet reduction. Platelet concentration is measured 15 hours after PLAG treatment. For comparison, olive oil and PBS are used instead of PLAG as controls, respectively for the Tamoxifen and lipopolysaccharide experiment. The results are shown in Tables 2 and 3.

TABLE 2

|  | normal | Tam + oil treated Control group (after 15 hours) | Tam + PLAG (5 mg/kg) treated group (after 15 hours) |
|---|---|---|---|
| Platelet Conc. (k/ul) | 1015.7 ± 33.5 | 459 ± 171.1 | 780.7 ± 195.9 |

TABLE 3

|  | normal | LPS + PBS | LPS + PLAG (1 mg/kg) | LPS + PLAG (2 mg/kg) |
|---|---|---|---|---|
| Platelet Conc. (k/ul) | 1005.50 ± 140.7 | 423.33 ± 55.2 | 450.00 ± 101.8 | 553.33 ± 42.0 |

The normal platelet concentration is 400 to 1600 k/μl and it can vary depending on environment. Tables 1-3 shows that when anemia is induced artificially by the administration of these compounds, the platelet concentration in the blood decreases and upon administration of PLAG to these patients, the platelet concentration is recovered.

Example 5—Effect of PLAG on Levels of Neutrophils Relative to Other Leukocytes in Mice Neutrophils and Lymphocytes:
To observe the ratio of neutrophil and lymphocyte in the blood of Balb/C mice, 1 mg/kg of lipopolysaccharide (LPS) is injected to mice, i.p. to induce inflammation. 5 mg/kg of PLAG is administered to the mice orally and blood samples are taken at 3 and 13 days after. In addition, for comparison, normal mice that are not treated with PLAG, receive PBS (phosphate buffered saline) and olive oil. The blood samples taken from the mice are treated with EDTA bottle 0.5 ml (Minocollect tube, Greiner bio-one, Austria) and the level of neutrophils (NEU) and lymphocytes (LYM) as a percentage of total leukocytes is measured using automated blood sample analyzer BC-6800 (Mindray, Shenzhen, China). As shown in Table 4, the relative level of neutrophils increased in response to LPS and even more in response to LPS+PLAG.

TABLE 4

|  | normal | LPS + PBS Treated control group | LPS + oil Treated control group | LPS + PLAG Treated group |
|---|---|---|---|---|
| Neutrophil Ratio (%) | 16.4 ± 0.1 | 36.9 ± 10.3 | 36.2 ± 3.2 | 53.2 ± 6.3 |
| Lymphocyte ratio (%) | 79.7 ± 1.9 | 50.9 ± 15.5 | 49.7 ± 2.2 | 34.6 ± 7.0 |

Monocytes:
Except for using C57BL/6 mouse instead of Balb/C mouse, mice are treated in the same manner as Example 6, the monocyte ratio (Mono) to total leukocytes is measured and the results are shown in Table 5.

TABLE 5

|  | normal | LPS + PBS Treated control group | LPS + oil Treated control group | LPS + PLAG Treated group |
|---|---|---|---|---|
| Monocyte ratio (%) | 1.9 ± 0.2 | 2.0 ± 2.4 | 1.6 ± 0.8 | 18.4 ± 6.6 |

Ratio of Neutrophil, Lymphocyte and Eosinophil after Treatment of Tamoxifen and PLAG:

100 mg/kg of anticancer agent Tamoxifen (Tam) is used to induce reduction of neutrophils, followed by treated with 5 mg/kg of PLAG and the ratios of neutrophil (NEU), lymphocyte (LYM), and eosinophil (EOS) are measured after 15 hours as in the previous experiment. The result is presented in Table 6.

TABLE 6

|  | normal | Tam + oil Treated control group | Tam + PLAG Treated group |
|---|---|---|---|
| Neutrophil Ratio (%) | 39.9 ± 7.4 | 25.1 ± 8.0 | 35.2 ± 2.4 |
| Eosinophil Ratio (%) | 3.9 ± 1.3 | 6.4 ± 4.0 | 15.1 ± 0.3 |
| Lymphocyte ratio (%) | 49.6 ± 7.3 | 66.4 ± 8.8 | 45.7 ± 4.1 |

Even though the concentration of each leukocyte can be changed depending on the subject conditions, in the present experiments, normal range of neutrophil ratio in leukocyte is 7-50% and lymphocyte ratio is 42-92%. As seen in Tables 4 and 5, upon treatment of LPS and PLAG, neutrophil and monocyte ratios increased significantly, while lymphocyte ratio decreased. Table 6 shows that PLAG generally maintains the normal ratios of neutrophil, lymphocyte and eosinophil against tamoxifen challenge.

Example 6—Efficacy of PLAG on Reducing Migration of Neutrophils

Mice are injected with bacterial lipopolysaccharide (LPS) to provoke an inflammatory response, in the presence or absence of PLAG:

TABLE 7

|  | Control | LPS only | LPS + PLAG |
|---|---|---|---|
| Neutrophil count (k/μl) in blood | 1.12 | 1.25 | 3.41 |
| Neutrophil count (k/μl) in lymph | 1.44 | 3.24 | 1.48 |

While PLAG enhances neutrophil levels in the blood, it inhibits migration to the lymph node.

Example 7—Efficacy of PLAG in Combination with G-CSF in Mouse Model

Mice receive cyclophosphamide (100 mpk, i.p.) for a period of ten days, with or without G-CSF (0.25 mpk, i.p.) or G-CSF (0.25 mpk, i.p.) plus PLAG (25 mpk, p.o.):

TABLE 7

|  | Cyclophosphamide only | G-CSF | G-CSF + PLAG |
|---|---|---|---|
| White blood cells (WBCs)(k/µl) | 3.34 | 5.37 | 8.68 |
| Neutrophils (k/µl) | 2.39 | 4.36 | 7.45 |

The dosage of G-CSF in this experiment is an effective dosage, and there is an upper limit on the effect of G-CSF, irrespective of dosage, as well as an upper level due to side effects. In this experiment, PLAG provides an increase of more than 60% WBC and more than 70% neutrophils over G-CSF alone. PLAG plus G-CSF thus provides a benefit greater than can be achieved with G-CSF alone, which is a surprising and important new technical effect. The addition of PLAG to G-CSF brings white blood cell and neutrophil levels to the levels of untreated mice, providing substantially complete protection from cyclophosphamide-induced neutropenia.

Example 8—Clinical Study: Activity of PLAG on Complement 3

Figure 7:
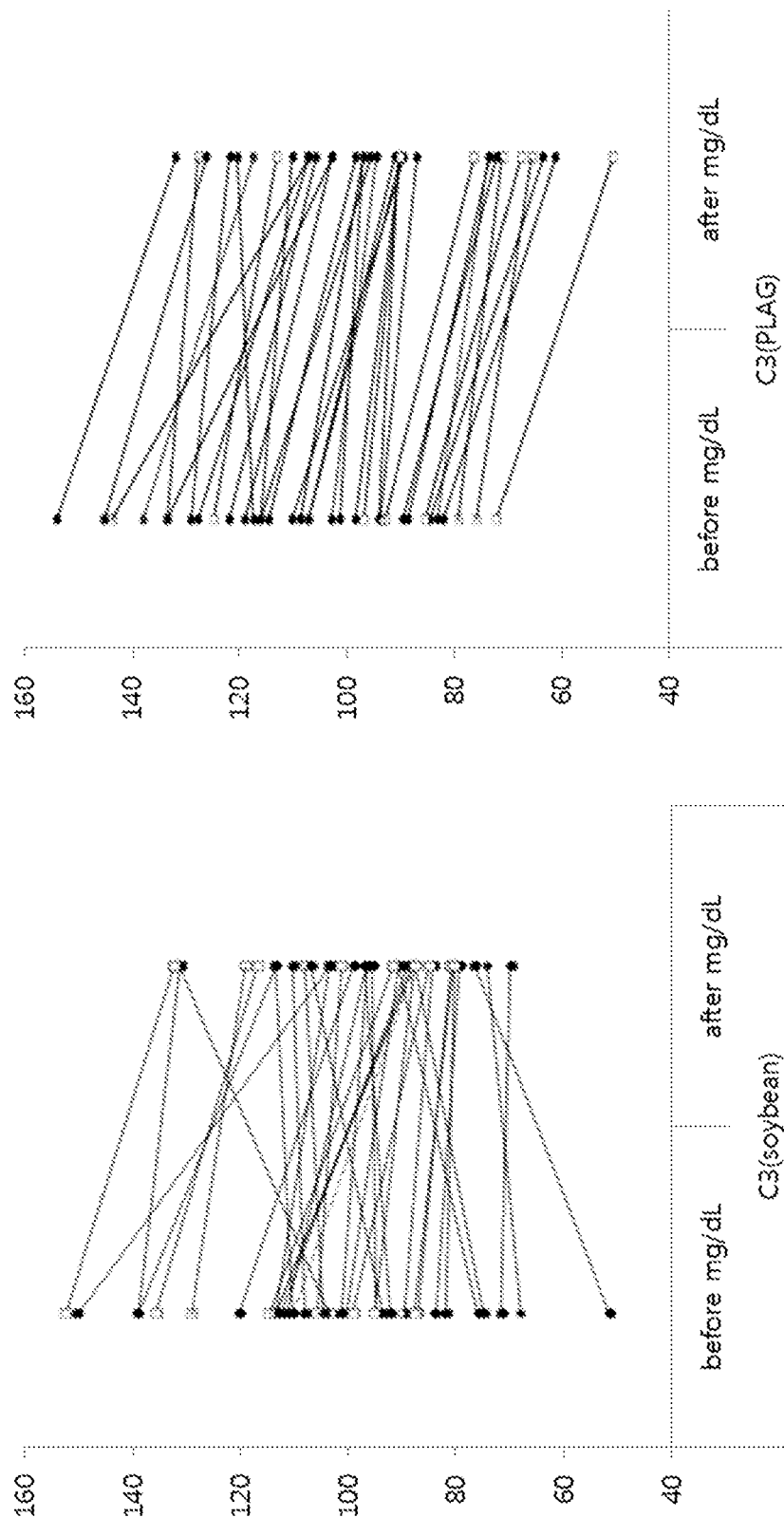
FIG. 7 depicts the results of a clinical trial on the activity of PLAG on Complement 3.

A clinical study is conducted in Gwandong University MyungJi Hospital Clinical Study Center in Republic of Korea with 27 healthy patients to study immune-modulating effect of PLAG. Volunteers are tested for 30 days in vivo as oral administer (500 mg of PLAG per day) under a legitimate clinical approval. Complement 3 is counted using C3 assay kit. The analysis result is shown in FIG. 7, and change of immunoactivity by the administration of PLAG in healthy subjects is shown in Table 8 (effect of PLAG supplementation on immune function of peripheral blood after 4-wk intervention). As shown in FIG. 7 and Table 8, the majority of those who consume PLAG for a month (twenty-six (26) subjects out of 27 patients) show decreased complement 3 (C3), while the control group, who are treated with soybean oil, show both increase and decrease of C3. The average concentration of C3 in blood shows a decrease of about 10 mg/dL after administration of PLAG with p value of <0.001.

TABLE 8

|  | Control (n = 22) | | | PLAG (n = 27) | | |
|---|---|---|---|---|---|---|
|  | Before | After | P value | Before | After | P-value |
| C3, mg/dl | 102.6 ± 22.5 | 97.5 ± 13.4 | 0.131 | 109.5 ± 13.0 | 99.7 ± 12.4 | <0.001 |
| C4, mg/dl | 19.6 ± 5.7 | 19.6 ± 5.5 | 0.927 | 21.6 ± 6.6 | 20.8 ± 5.6 | 0.187 |

Example 9—Pilot Study: Activity of PLAG on Thrombocytopenia and Neutropenia in Patients Receiving Chemotherapy PLAG is administered to sixteen pancreatic cancer patients after chemotherapy. The subjects of this study are unoperable pancreatic cancer patients with ECOG (Eastern Cooperative Oncology Group) performance status of "0" or "1", i.e. patients in good physical condition without much pain, able to enjoy almost normal lifestyle and thus, eligible for anticancer treatment for at least 2 months. The pancreatic cancer patients are "locally advanced" patients having tumor metastasis to the major vessels around pancreas or "Distant metastasis" patients with distant metastasis to liver, lung, bone, etc. ECOG performance status "0" refers to a patient who is asymptomatic, fully active, able to carry on all predisease activities without restriction with no pain and no problem for normal lifestyle, while "1" refers to a patient who is symptomatic but completely ambulatory with mile pain and a little problem for normal life. Anticancer (Gemcitabine and Erlotinib combo treatment) Regimen is as follows: 1,000 mg of Gemcitabine is injected once a week for three weeks (Day 1, Day 8, Day 15), and is not injected in the next one week (Day 22). Therefore, 1 cycle of anticancer treatment requires 1 month. 100 mg of Erlotinib (Tarceva) is administered once per day everyday orally. 1,000 mg of PLAG is also administered once per day orally, starting from 3 days before anticancer treatment until the last chemotherapy treatment. The PLAG treatment group and control group both completed two cycles of anticancer treatment. There is no difference among the control and PALG treatment groups in the amount or schedule of anti-cancer treatment.

Effect on Platelets:

In the PLAG treatment group, there is no patient for whom the anticancer treatment needs to be postponed or the dose needed to be adjusted due to platelet number decrease to less than 50,000/µl. In PLAG treatment group, there is also no patient whose platelet number dropped to less than 25,000/µl, meaning clinically a high risk of bleeding. Among the 16 patients in PLAG treatment group, 7 patients (43.8%) have >50% decrease in platelet count, 4 patients (25%) have >60% decrease, and none have >70% decrease.

Figure 8:
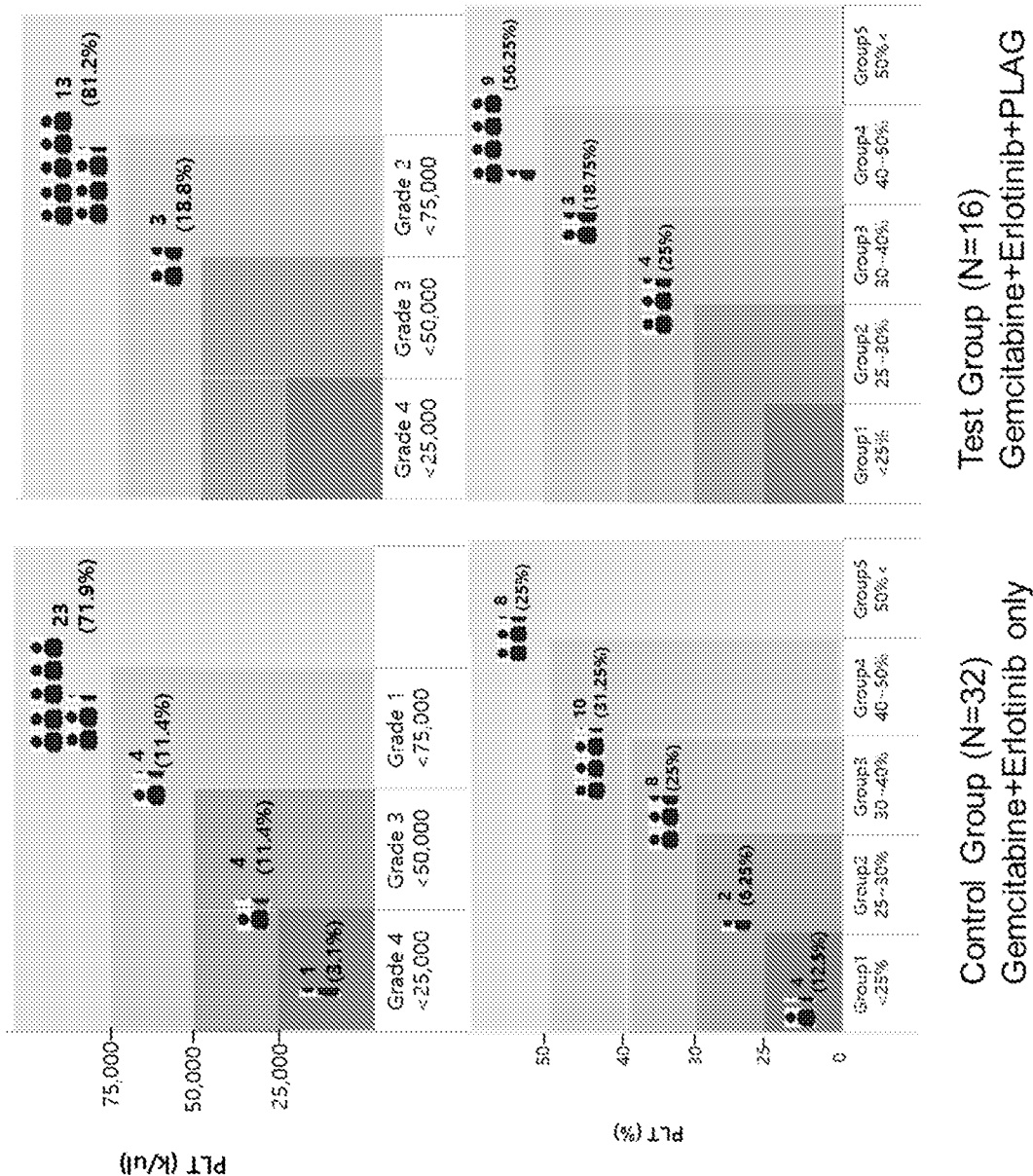
FIG. 8 depicts chemotherapy drug-induced thrombocytopenia (CIN) inhibited by PLAG treatment in a clinical trial.

In the control group, 5 patients (15.6%) among those who received anticancer treatment have a platelet number of <50,000 with high risk of bleeding, meaning that anticancer treatment would need to be postponed or the dose adjusted, and 1 patient (3.1%) has platelet decrease to <25,000/µl, presenting a serious risk of critical internal bleeding. 24 patients (75%) have platelet decrease of more than 50%, 14 patients (43.8%) have platelet decrease of more than 60%, 6 patients (18.8%) have platelet decrease of more than 70%, and 4 patients (12.5%) have platelet decrease of more than 75% (See FIG. 8).

Effect on Neutrophils:

In the PLAG treatment group, 6 patients (37.5%) have neutrophil (Absolute Neutrophil Count: ANC) decrease to less than 1,500/µl; 3 patients (18.8%) have neutrophil decrease to less than 1,000/µl; none decreases to less than 500/µl; 6 patients (37.5%) have neutrophil number decrease to less than 50%; 3 patients (18.8%) have neutrophil number decrease to less than 60%, and none have neutrophil number decrease to less than 75%.

Figure 9:
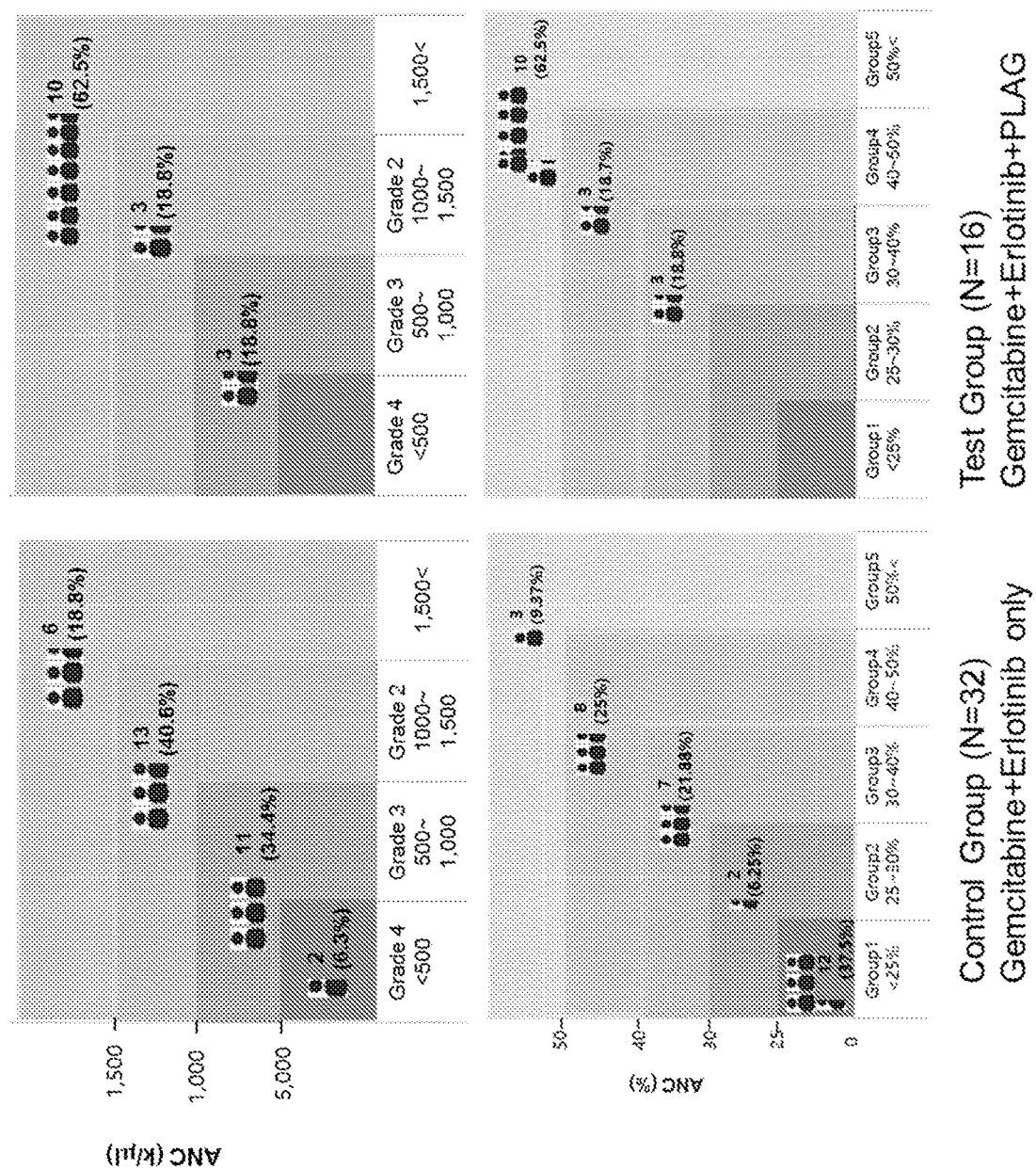
FIG. 9 depicts chemotherapy drug-induced neutropenia (CIN) inhibited by PLAG treatment in a clinical trial.

In the control group, 26 patients (81.3%) have neutrophil decrease to less than 1,500/µl; 13 patients (40.6%) have neutrophil decrease to less than 1,000/µl; 2 patients (6.3%) have neutrophil decrease to less than 500 so the anticancer treatments have to be stopped for the patients; 29 patients (90.6%) have neutrophil decrease of more than 50%; 21 patients (65.6%) have neutrophil decrease of more than 60%; and 12 patients (37.5%) have neutrophil decrease of more than 75% (See FIG. 9). In the control group, 26 patients (81.3%) are found to have a high risk of infection during anticancer treatment with neutrophil number of less than 1,500, but in PLAG treatment group, only 6 patients (37.5%) are found to have high risk of infection with neutrophil number of less than 1,500, thus confirming the effectiveness of PLAG. Also, while the anticancer treatment causes a 75% reduction of neutrophils for 12 patients (37.5%) in the control group, there is not one patient having 75% reduction of neutrophil in PLAG treatment group.

This pilot trial has a statistically meaningful p-value of <0.05 between the treatment and control groups. The results show that the levels of neutrophil and platelet are reduced by the chemotherapy in both groups, but significantly less in the PLAG group. Not only are the patients in the PLAG group at lower risk for thrombocytopenia and neutropenia, but they are consequently better able to complete their chemotherapy, meaning they would be expected to have a better chance of surviving cancer. Thus, the result shows that PLAG is highly effective for the treatment and management of thrombocytopenia and leukopenia in cancer patients receiving chemotherapy.

Example 10—Unit Dosage Formulation

An exemplary soft gelatin capsule for use in the methods described herein, containing (i) PLAG and (ii) α-tocopherol, is prepared, having a composition as follows:

TABLE 9

Composition of PLAG Softgel Capsules

| Component | Function | Unit Formula |
|---|---|---|
| PLAG | Active Ingredient | 500.0 mg |
| α-tocopherol | Anti-oxidant | 1.0 mg |

TABLE 10

Composition of Soft Capsule Shells

| Ingredients | Function |
|---|---|
| Gelatin | Capsule shell |
| Concentrated glycerin | Plasticizer |
| Methyl para-oxybenzoate | Preservative |
| Propyl para-oxybenzoate | Preservative |
| Ethyl vanillin | Flavor |
| Titanium dioxide | Colorant |
| Tar color, MFDS notified Blue No. 1 | Colorant |
| Tar color, MFDS notified Red No. 40 | Colorant |
| Tar color, MFDS notified Yellow No. 203 | Colorant |
| Purified water | Vehicle |

The invention claimed is:

1. A method for treating chemotherapy-induced thrombocytopenia, comprising administering to a human in need thereof an effective amount of a compound of Formula 2:

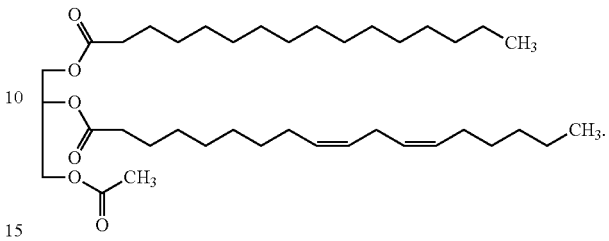

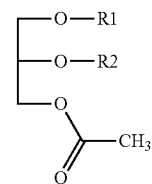

2. The method of claim 1, wherein the compound of Formula 2 is administered in a pharmaceutical composition, which is substantially free of other monoacetyl diacyl glycerol compounds.

3. The method of claim 1, wherein the compound of Formula 2 is administered in a pharmaceutical composition, which is substantially free of triglyceride compounds.

4. The method of claim 1, wherein human is suffering from myelosuppressive chemotherapy-induced thrombocytopenia.

5. The method of claim 4 the myelosuppressive chemotherapy-induced thrombocytopenia is caused by a drug selected from among Ziv-aflibercept, Brentuximab vedotin, Pralatrexate, Ganciclovir, Valganciclovir, Romidepsin, Ruxolitinib, Decitabine, Imatinib, Topotecan, Lenalidomide, Irinotecan, Interferons, Phenylhydrazine, Tamoxifen, Lipopolysaccharide, Anthracycline antibiotics, daunorubicin, doxorubicin, Gemcitabine, Cytoxan, Paclitaxel, Alkylating antineoplastic agent, DNA intercalating agent, Alkylating agent, bendamustin, mustard, Topoisomerase inhibitor, Bortezomib, Temsirolimus, Vorinostat, Ifosfamide, and Ixabepilone.

6. The method of claim 4, wherein the human receives a chemotherapeutic agent selected from one or more of cyclophosphamide, doxorubicin, etoposide, ifosfamide, mesna, cisplatin, gemcitabine, tamoxifen and lenalidomide.

7. The method of claim 4, wherein the human receives lenalidomide.

8. The method of claim 1, wherein the human has multiple myeloma, chronic myelogenous leukemia (CML), acute myeloid leukemia, or myelodysplastic syndrome.

9. The method of claim 1, further comprising administering a G-CSF to the patient.

10. The method of claim 9, wherein the patient suffers from thrombocytopenia due to treatment with one or more chemotherapeutic agents selected from cyclophosphamide, doxorubicin, etoposide, ifosfamide, mesna, cisplatin, gemcitabine, and tamoxifen.

11. The method of claim 9, wherein the G-CSF is selected from filgrastim, pegfilgrastim, and lenograstim.

12. The method of claim 1, wherein administering the compound suppresses upregulated or activated Complement 3 (C3).

13. The method of claim 1, wherein the compound is administered in the form of a pharmaceutical composition for oral administration.

14. The method of claim 1, wherein the compound is administered in the form of a pharmaceutical composition which is a soft gelatin capsule containing the compound in combination or association with a pharmaceutically acceptable diluent or carrier.

15. The method of claim 1, wherein the platelet count of the human does not decrease more than 70 percent.

16. The method of claim 1 wherein a platelet number of the human does not decrease to less than 50,000/µl.

17. The method of claim 1 wherein a platelet number of the human does not decrease to less than 25,000/µl.

18. The method of claim 1 wherein the human is identified as suffering from thrombocytopenia and the compound is administered to the identified human.

\* \* \* \* \*